United States Patent
Shieh

(10) Patent No.: US 9,724,279 B2
(45) Date of Patent: Aug. 8, 2017

(54) CORE-SHELL PARTICLES, PREPARATION PROCESS THEREOF, AND COMPOSITION CONTAINING THE SAME

(71) Applicant: Huai Cheng Lee, Taipei (TW)

(72) Inventor: Dar-Bin Shieh, Tainan (TW)

(73) Assignee: SYNEURX INTERNATIONAL CORP., Taipei (TW)

( * ) Notice: Subject to any disclaimer, the term of this patent is extended or adjusted under 35 U.S.C. 154(b) by 4 days.

(21) Appl. No.: 14/438,556

(22) PCT Filed: Oct. 28, 2013

(86) PCT No.: PCT/CN2013/086081
§ 371 (c)(1),
(2) Date: Apr. 24, 2015

(87) PCT Pub. No.: WO2014/063662
PCT Pub. Date: May 1, 2014

(65) Prior Publication Data
US 2015/0290092 A1 Oct. 15, 2015

Related U.S. Application Data

(60) Provisional application No. 61/718,942, filed on Oct. 26, 2012.

(51) Int. Cl.
| | | |
|---|---|---|
| A61K 8/21 | (2006.01) | |
| A61K 9/16 | (2006.01) | |
| A61K 9/51 | (2006.01) | |
| A61K 8/24 | (2006.01) | |
| A61Q 11/00 | (2006.01) | |
| A61Q 17/00 | (2006.01) | |
| A61K 8/81 | (2006.01) | |
| A61K 8/84 | (2006.01) | |
| A61K 8/02 | (2006.01) | |
| A61K 8/19 | (2006.01) | |
| A61K 8/20 | (2006.01) | |
| A61K 8/73 | (2006.01) | |
| A61K 9/50 | (2006.01) | |

(52) U.S. Cl.
CPC ............. *A61K 8/21* (2013.01); *A61K 8/0245* (2013.01); *A61K 8/0279* (2013.01); *A61K 8/19* (2013.01); *A61K 8/20* (2013.01); *A61K 8/24* (2013.01); *A61K 8/735* (2013.01); *A61K 8/8147* (2013.01); *A61K 8/84* (2013.01); *A61K 9/1635* (2013.01); *A61K 9/1641* (2013.01); *A61K 9/5073* (2013.01); *A61K 9/5084* (2013.01); *A61K 9/5115* (2013.01); *A61K 9/5138* (2013.01); *A61K 9/5146* (2013.01); *A61K 9/5161* (2013.01); *A61Q 11/00* (2013.01); *A61Q 17/005* (2013.01); *A61K 9/5078* (2013.01); *A61K 2800/413* (2013.01); *A61K 2800/594* (2013.01); *A61K 2800/62* (2013.01); *A61K 2800/63* (2013.01); *A61K 2800/651* (2013.01); *A61K 2800/654* (2013.01)

(58) Field of Classification Search
None
See application file for complete search history.

(56) References Cited

U.S. PATENT DOCUMENTS

| | | | | |
|---|---|---|---|---|
| 2006/0293396 | A1* | 12/2006 | Bringley | A61K 9/146 516/100 |
| 2008/0223578 | A1* | 9/2008 | Berkland | C09K 8/512 166/300 |
| 2008/0295737 | A1* | 12/2008 | Henglein | C09C 3/10 106/421 |
| 2009/0186093 | A1* | 7/2009 | Liu | A61K 9/5026 424/497 |
| 2011/0287247 | A1* | 11/2011 | Kawasaki | C08F 2/28 428/313.9 |

FOREIGN PATENT DOCUMENTS

| | | |
|---|---|---|
| CN | 101176726 A | 5/2008 |
| CN | 102091605 A | 6/2008 |
| CN | 101428220 A | 5/2009 |
| CN | 102319564 A | 1/2012 |
| KR | 20110034237 A | 4/2011 |

* cited by examiner

*Primary Examiner* — Susan Tran
(74) *Attorney, Agent, or Firm* — Muncy, Geissler, Olds & Lowe, P.C.

(57) ABSTRACT

Disclosed herein are core-shell particles and process for preparing the same. The core-shell particles include a functional core, a multilayer or porous shell surrounding the functional core and polymeric tails extending from the shell. The functional core includes an antimicrobial agent or an antitumor agent. Also disclosed herein are pharmaceutical or health care compositions containing the core-shell particles.

33 Claims, 10 Drawing Sheets

CORE-SHELL PARTICLES, PREPARATION PROCESS THEREOF, AND COMPOSITION CONTAINING THE SAME

CROSS-REFERENCE TO RELATED APPLICATION

This application claims priority to U.S. provisional application No. 61/718,942, filed Oct. 26, 2012, the entirety of which is incorporated herein by reference.

FIELD OF THE INVENTION

The present disclosure relates to core-shell particles; more particularly, to core-shell particles for use in healthcare or medical treatment.

DESCRIPTION OF RELATED ART

In recent years, intensive research attention has been drawn to the development of micro- or nano-scale particles capable of delivering active components to target site(s). Despite these efforts, significant challenges remain.

The maintenance and improvement of oral health is of great importance, for poor oral health may not only lead to various diseases (e.g., caries, gingivitis, and periodontitis) but also impair the aesthetics of teeth.

For example, dental caries (or tooth decay) is caused by bacterial infection. The most significant contributor to dental caries is *Steptococcus mutans*; the metabolism of this and other cariogenic microorganisms creates an acid environment that causes the demineralization of the hard tissues (such as enamel, dentin and cementum) of the teeth. Periodontal diseases, including gingivitis and periodontitis, are also caused by bacterial infection, and periodontopathic bacteria include *Porphyromonas gingivalis, Porphyromonas gingivalis, Tannerella forsythia, Campylobacter rectus* and *Treponema denticola*. The toxin released by these or other periodontopathic microorganisms leads to the initial destruction of the soft connective tissue and, eventually, to tooth loss because of the disruption of the underlying alveolar bone and ligament supporting the teeth.

One common way of preventing and/or treating dental caries and periodontal diseases is the use of antimicrobial agents that kill the pathogenic microorganisms or disrupts the metabolism thereof. For example, fluorides are incorporated into various oral care products or dental fillers, which are used as part of a personal or a professional oral care regimen. However, the antimicrobial agents tend to be washed off from the oral cavity due to saliva secretion or food ingestion, and hence shorten the exposure time of the targeted microorganism to the selected antimicrobial agent. Remineralization of the hard tissues is also an important strategy in combating dental conditions. Remineralization may be promoted by using calcium glycerophosphate in an oral care product. Accordingly, when designing micro- or nano-particles for oral use, there is an ongoing need for a novel material that prevents cariogenic conditions and remineralizes the demineralized enamel.

Additionally, micro- or nano-scale particles for carrying and delivering antitumor agents to various tumor lesions are also being investigated. In designing these particles, it is important to consider the drug load, drug release profile and tumor-specificity of the particles.

Micro- and nano-particles are also useful in the treatment of infections. As could be appreciated, the metabolism of the pathogenic microorganisms may affect the physical and/or chemical property of the infected area. For example, the pH value in the infected area may different from the normal area. Hence, it is desirable to design particles that are sensitive to one or more environmental factors, such as, the temperature, pH, concentration of a specific metabolite, etc.

Despite the advances in the field of drug development, there is a need in the related field to provide a micro- or nano-particles that address the problem or insufficiency existed in the prior art.

SUMMARY

The following description presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

In the first aspect, the present disclosure is directed to a multilayer core-shell particle. The multilayer core-shell particle comprises a functional core, one or more composite shell layers, an outermost shell layer and a plurality of polymeric tails. The multilayer core-shell structure allows the controlled release of the active agent in the functional core from the multilayer core-shell particle. For example, the release rate or release level of the active agent may be controlled by varying the numbers of the composite shell layers. Alternatively or additionally, the release profile thereof may depend on the selection of the materials constituting the shell(s).

According to one embodiment of the present disclosure, the one or more composite shell layers encapsulate the functional core, and each composite shell layer comprises a first polymeric layer, a plurality of first di- or trivalent ion-containing nanoparticles, a second polymeric layer and a third polymeric layer. Structurally, the first polymeric layer encapsulates the functional core, the plurality of first di- or trivalent ion-containing nanoparticles adhering onto the outer surface of the first polymeric layer, the second polymeric layer covers the first polymeric layer and the plurality of di- or trivalent ion-containing nanoparticles, and the third polymeric layer encapsulates the second polymeric layer. Further, the outermost shell layer comprises a fourth polymeric layer that encapsulates the one or more composite shell layers, and a plurality of second di- or trivalent ion-containing nanoparticles adhering onto the outer surface of the fourth polymeric layer, while the plurality of polymeric tails extend from the outer surface of the outermost shell layer. Both of the first and second polymeric layers are made of a first polymer that is oppositely charged to the functional core; the third polymeric layer is made of a second polymer that is oppositely charged to the first polymer, while the fourth polymeric layer is made of a third polymer that has the same charge as the first polymer. The polymeric tails comprise a fourth polymer that can be a cationic, anionic or neutral polymer.

According to one embodiment of the present disclosure, the multilayer core-shell particle comprises 2 to 40 composite shell layers.

In various embodiments of the present disclosure, the functional core comprises an active agent which is an antimicrobial agent of sodium fluoride, calcium fluoride, acidulated phosphate fluoride, stannous fluoride, triclosan, chlorhexidine, amikacin, gentamicin, kanamycin, neomycin, netilmicin, tobramycin, paromomycin, spectinomycin, geldanamycin, herbimycin, rifaximin, streptomycin, loracarbef, ertapenem, doripenem, imipenem, cilastatin, meropenem, cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole, teicoplanin, vancomycin, telavancin, clindamycin, lincomycin, daptomycin, azithromycin, clarithromycin, dirithromycin, erythromycin, roxithromycin, troleandomycin, telithromycin, spiramycin, aztreonam, furazolidone, nitrofurantoin, linezolid, posizolid, radezolid, torezolid, amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, penicillin G, temocillin, ticarcillin, clavulanate, sulbactam, tazobactam, bacitracin, colistin polymyxin B, ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfamethoxazole, sulfanilimide, sulfasalazine, sulfisoxazole, trimethoprim-sulfamethoxazole, sulfonamidochrysoidine, demeclocycline, doxycycline, minocycline, oxytetracycline, tetracycline, clofazimine, dapsone, capreomycin, cycloserine, ethambutol, ethionamide, isoniazid, pyrazinamide, rifampicin, rifabutin, rifapentine, streptomycin, arsphenamine, chloramphenicol, fosfomycin, fusidic acid, metronidazole, mupirocin, platensimycin, quinupristin, dalfopristin, thiamphenicol, tigecycline, tinidazole and trimethoprim.

According to certain embodiments of the present disclosure, the functional core comprises an active agent which is a whitening agent of, hydrogen peroxide, carbamide peroxide, and zinc oxide.

Alternatively, the functional core comprises an active agent which is an antitumor agent, such as actinomycin, all-trans retinoic acid, alitretinoin, azacitidine, azathioprine, bevacizumab, bexarotene, bleomycin, bortezomib, carboplatin, capecitabine, cetuximab, cisplatin, chlorambucil, cyclophosphamide, cytarabine, daunorubicin, docetaxel, doxifluridine, doxonthicin, epirubicin, epothilone A-F, erlotinib, etoposide, fluorouracil, gemcitabine, gefitinib, hydroxyurea, idarubicin, imatinib, ipilimumab, irinotecan, mechlorethamine, melphalan, mercaptopurine, methotrexate, mitoxantrone, ocrelizumab, ofatumumab, oxaliplatin, paclitaxel, panitumab, pemetrexed, rituximab, romidepsin, tafluposide, teniposide, tioguanine, topotecan, tretinoin, valrubicin, vemurafenib, vinblastine, vincristine, vindesine, vinorelbine, vismodegib, and vorinostat. According to embodiments of the present disclosure, the first and second di- or trivalent ion-containing nanoparticles respectively comprise a material selected from the group consisting of hydroxyapatite, fluoroapatite, calcium phosphate, calcium fluoride, zinc oxide, silicate, titanium oxide and a combination thereof.

According to certain embodiments of the present disclosure, at least one of the first, second and third polymers is a cationic polymer which can be polyarginine, polylysine, polyhistidine, poly-ornithine, polyethyleneimine, polypropyleneimine, poly(allylamine), polystyrene-maleic acid, gelatin or chitosan.

In some embodiments of the present disclosure, at least one of the first, second and third polymers is an anionic polymer, which can be polyacrylic acid, polymethacrylic acid, polycrotonic acid, polyaspartic acid, polyglutamic acid, polylactic acid, poly(lactic-co-glycolic) acid, hyaluronic acid, alginic acid, polystyrene sulfonate, carrageenan, poly(methylene-co-guanidine), polyphosphoric acid, or pamidronic acid.

According to various embodiments of the present disclosure, the fourth polymer is a cationic, anionic or neutral polymer. Non-limiting examples of polymers suitable for use herein include, polyarginine, polylysine, polyhistidine, poly-ornithine, polyethyleneimine, polypropyleneimine, poly(allylamine), polystyrene-maleic acid, gelatin, chitosan, polyacrylic acid, polymethacrylic acid, polycrotonic acid, polyaspartic acid, polyglutamic acid, polylactic acid, poly(lactic-co-glycolic) acid, hyaluronic acid, and alginic acid, polystyrene sulfonate, carrageenan, poly(methylene-co-guanidine), polyphosphoric acid, or pamidronic acid, xanthan gum, polycarbophil, poly(methylvinyl ether-co-maleic anhydride), shellac, agar, pectin, polyvinyl acetate phthalate, guar gum, polyethylene glycol, dextrin, polydextrose, and polyethylene oxide.

In certain embodiments of the present disclosure, the one or more composite shell layers and the outermost shell have a total thickness of about 0.5 to 1,000 nm.

According to some embodiments of the present disclosure, the average diameter of the multilayer core-shell particle is about 50 to 50,000 nm.

In various embodiments of the present disclosure, the multilayer core-shell particle has a cubic shape, needle shape, spherical shape, pyramidal shape or polygonal cylindrical shape.

According to certain embodiments of the present disclosure, the multilayer core-shell particle is a pH-sensitive particle so that the release of the active agent from the multilayer core-shell particle is dependent on the pH of the surrounding environment.

According to embodiments of the present disclosure, the functional core comprises sodium fluoride; the first, third and fourth polymers are polyacrylic acid; the second polymer is polyethyleneimine; the first and second di- or trivalent ion-containing nanoparticles are composite nanoparticles made of hydroxyapatite, fluoroapatite and calcium fluoride; and there are 4 to 10 composite shell layers.

In the second aspect, the present disclosure is directed to a process for preparing the multilayer core-shell particle according to the first aspect and related embodiments of the present disclosure.

According to one embodiment of the present disclosure, the preparation process comprises the following steps:
(a) forming the one or more composite shell layers encapsulating the functional core, wherein each composite shell layer is formed by the steps of,
  (a1) mixing the functional core with a first polymer to form a first particle, wherein the first particle has a first polymeric layer of the first polymer and encapsulates the functional core, and the first polymer and the functional core are oppositely-charged,
  (a2) mixing the first particle with a plurality of first di- or trivalent ion-containing nanoparticles to form a second particle, wherein the second particle has the first di- or trivalent ion-containing nanoparticles adhering onto the outer surface of the first particle,
  (a3) mixing the second particle with the first polymer to form a third particle, wherein the third particle has a second polymeric layer of the first polymer and encapsulates the second particle, and
  (a4) mixing the third particle with a second polymer to form a fourth particle, wherein the fourth particle has a third polymeric layer of the second polymer and encapsulates the third particle, and the first polymer and the second polymer are oppositely-charged;

(b) forming the outermost shell layer encapsulating the one or more composite shell layers by the steps of,
- (b1) mixing the fourth particle with a third polymer to form a fifth particle, wherein the fifth particle has a fourth polymeric layer of the third polymer and encapsulates the fourth particle, and the third polymer has the same charge as the first polymer, and
- (b2) mixing the fifth particle with a plurality of second di- or trivalent ion-containing nanoparticles to form a sixth particle, wherein the sixth particle has the plurality of second di- or trivalent ion-containing nanoparticles adhering onto the outer surface of the fourth polymeric layer; and (c) forming the plurality of polymeric tails extending from the outer surface of the outermost shell layer by mixing the sixth particle with a fourth polymer under stirring, wherein the fourth polymer is cationic, anionic or neutral polymer.

According to various embodiments of the present disclosure, the step (a) is repeated 2 to 40 times before the step (b) is performed and thereby forms 2 to 40 composite shell layers.

In the third aspect, the present invention is directed to a porous core-shell particle. The porous core-shell particle comprises a functional core, porous ceramic shell and a plurality of polymeric tails. The porous core-shell structure allows the controlled release of the active agent in the functional core from the porous core-shell particle. For example, the release rate of the active agent may be controlled by varying the thickness of the porous ceramic shell or the composition making up the porous ceramic shell.

According to one embodiment of the present invention, the porous ceramic shell encapsulates the functional core while the plurality of polymeric tails respectively extend from the outer surface of the porous ceramic shell. The porous ceramic shell is made of a material selected from the group consisting of hydroxyapatite, fluoroapatite, calcium phosphate, calcium fluoride, zinc oxide, silicate, titanium oxide and a combination thereof.

In various embodiments of the present disclosure, the functional core comprises an active agent which is an antimicrobial agent of sodium fluoride, calcium fluoride, acidulated phosphate fluoride, stannous fluoride, triclosan, chlorhexidine, amikacin, gentamicin, kanamycin, neomycin, netilmicin, tobramycin, paromomycin, spectinomycin, geldanamycin, herbimycin, rifaximin, streptomycin, loracarbef, ertapenem, doripenem, imipenem, cilastatin, meropenem, cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole, teicoplanin, vancomycin, telavancin, clindamycin, lincomycin, daptomycin, azithromycin, clarithromycin, dirithromycin, erythromycin, roxithromycin, troleandomycin, telithromycin, spiramycin, aztreonam, furazolidone, nitrofurantoin, linezolid, posizolid, radezolid, torezolid, amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, penicillin G, temocillin, ticarcillin, clavulanate, sulbactam, tazobactam, bacitracin, colistin polymyxin B, ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfamethoxazole, sulfanilimide, sulfasalazine, sulfisoxazole, trimethoprim-sulfamethoxazole, sulfonamidochrysoidine, demeclocycline, doxycycline, minocycline, oxytetracycline, tetracycline, clofazimine, dapsone, capreomycin, cycloserine, ethambutol, ethionamide, isoniazid, pyrazinamide, rifampicin, rifabutin, rifapentine, streptomycin, arsphenamine, chloramphenicol, fosfomycin, fusidic acid, metronidazole, mupirocin, platensimycin, quinupristin, dalfopristin, thiamphenicol, tigecycline, tinidazole and trimethoprim.

According to certain embodiments of the present disclosure, the functional core comprises an active agent which is a whitening agent of, hydrogen peroxide, carbamide peroxide, and zinc oxide.

Alternatively, the functional core comprises an active agent which is an antitumor agent such as actinomycin, all-trans retinoic acid, alitretinoin, azacitidine, azathioprine, bevacizumab, bexarotene, bleomycin, bortezomib, carboplatin, capecitabine, cetuximab, cisplatin, chlorambucil, cyclophosphamide, cytarabine, daunorubicin, docetaxel, doxifluridine, doxorubicin, epirubicin, epothilone A-F, erlotinib, etoposide, fluorouracil, gemcitabine, gefitinib, hydroxyurea, idarubicin, imatinib, ipilimumab, irinotecan, mechlorethamine, melphalan, mercaptopurine, methotrexate, mitoxantrone, ocrelizumab, ofatumumab, oxaliplatin, paclitaxel, panitumab, pemetrexed, rituximab, romidepsin, tafluposide, teniposide, tioguanine, topotecan, tretinoin, valrubicin, vemurafenib, vinblastine, vincristine, vindesine, vinorelbine, vismodegib, and vorinostat.

According to certain embodiments of the present disclosure, the plurality of polymeric tails comprise a cationic, anionic or neutral polymer. Non-limiting examples of polymers suitable for use herein include, polyarginine, polylysine, polyhistidine, poly-ornithine, polyethyleneimine, polypropyleneimine, poly(allylamine), polystyrene-maleic acid, gelatin, chitosan, polyacrylic acid, polymethacrylic acid, polycrotonic acid, polyaspartic acid, polyglutamic acid, polylactic acid, poly(lactic-co-glycolic) acid, hyaluronic acid, and alginic acid, polystyrene sulfonate, carrageenan, poly(methylene-co-guanidine), polyphosphoric acid, or pamidronic acid, xanthan gum, polycarbophil, poly(methylvinyl ether-co-maleic anhydride), shellac, agar, pectin, polyvinyl acetate phthalate, guar gum, polyethylene glycol, dextrin, polydextrose, and polyethylene oxide.

In certain embodiments of the present disclosure, the porous ceramic shell has a thickness of about 0.5 to 1,000 nm.

According to some embodiments of the present disclosure, the average diameter of the porous core-shell particle is about 50 to 50,000 nm.

In various embodiments of the present disclosure, the porous core-shell particle has a cubic shape, needle shape, spherical shape, pyramidal shape or polygonal cylindrical shape.

According to certain embodiments of the present disclosure, the porous core-shell particle is a pH-sensitive particle so that the release of the active agent from the porous core-shell particle is dependent on the pH of the surrounding environment.

In one embodiment, the functional core comprises sodium fluoride; the porous ceramic shell is made of hydroxyapatite, fluoroapatite and calcium fluoride; and the plurality of polymeric tails comprise polyacrylic acid.

In the fourth aspect, the present disclosure is directed to a process for preparing a porous core-shell particle according to the third embodiments and related embodiments.

According to one embodiment of the present disclosure, the preparation process comprises the following steps:
  (a) forming one or more composite shell layers encapsulating the functional core, wherein each composite shell layer is formed by the steps of,
    (a1) mixing the functional core with a first polymer o form a first particle, wherein the first particle has a first polymeric layer of the first polymer and encapsulates the functional core, and the first polymer and the functional core are oppositely-charged,
    (a2) mixing the first particle with a plurality of first di- or trivalent ion-containing nanoparticles to form a second particle, wherein the second particle has the first di- or trivalent ion-containing nanoparticles adhering onto the outer surface of the first particle,
    (a3) mixing the second particle with the first polymer to form a third particle, wherein the third particle has a second polymeric layer of the first polymer and encapsulates the second particle, and
    (a4) mixing the third particle with a second polymer to form a fourth particle, wherein the fourth particle has a third polymeric layer of the second polymer and encapsulates the third particle, and the first polymer and the second polymer are oppositely-charged;
  (b) forming an outermost shell layer encapsulating the one or more composite shell layers by the steps of,
    (b1) mixing the fourth particle with a third polymer to form a fifth particle, wherein the fifth particle has a fourth polymeric layer of the third polymer and encapsulates the composite shell layer, and the third polymer has the same charge as the first polymer, and
    (b2) mixing the fifth particle with a plurality of second di- or trivalent ion-containing nanoparticles to form a sixth particle, wherein the sixth particle has the plurality of second di- or trivalent ion-containing nanoparticles adhering onto the outer surface of the fifth particle;
  (c) forming the porous ceramic shell encapsulating the outer surface of the functional core by sintering the sixth particle at a temperature of 200° C. to 800° C. to form a seventh particle; and
  (d) forming the plurality of polymeric tails respectively extending from the outer surface of the porous ceramic shell by mixing the seventh particle with a fourth polymer, wherein the fourth polymer is a cationic, anionic or neutral polymer.

According to various embodiments of the present disclosure, the step (a) is repeated 2 to 40 times before the step (b) is performed.

In one embodiment, the functional core comprises sodium fluoride; the first, third and fourth polymers are polyacrylic acid; the second polymer is polyethyleneimine; the first and second di- or trivalent ion-containing nanoparticles are composite nanoparticles made of hydroxyapatite, fluoroapatite and calcium fluoride.

In the fifth aspect, the present disclosure is directed to a pharmaceutical or health care composition comprising the above-mentioned multilayer core-shell particles or porous core-shell particles.

In various embodiments, the present pharmaceutical or health care composition comprises an effective amount of the multilayer core-shell particles according to the first aspect and related embodiment of the present disclosure, and a pharmaceutically acceptable excipient.

According to other embodiments of the present disclosure, the present pharmaceutical or health care composition comprises an effective amount of the porous core-shell particles according to the third aspect and related embodiment of the present disclosure, and a pharmaceutically acceptable excipient.

In some embodiments, said pharmaceutical or health care composition is an oral care composition. The present oral care composition is advantageous in that it possesses any of the following properties: (1) the multilayer core-shell particles and the porous core-shell particles have polymeric tails capable of adhering onto the enamel or other hard tissues of teeth; (2) the multilayer and the porous core-shell structure allow a pH-dependent release of active agent; (3) the multilayer and the porous core-shell structure allow a sustained release of active agent; and (4) the core-shell particles exhibit dual functionalities of antimicrobial activity and remineralization.

In this case, the functional cores of multilayer or porous pore-shell particles may comprise an antimicrobial agent of sodium fluoride, calcium fluoride, acidulated phosphate fluoride, stannous fluoride, triclosan, and chlorhexidine.

Additionally or alternatively, the functional cores of multilayer or porous pore-shell particles may comprise a whitening agent of, hydrogen peroxide, carbamide peroxide, and zinc oxide.

In certain embodiments, said pharmaceutical or health care composition is an antimicrobial composition in which the functional core of the multilayer or porous core-shell particle comprises an antimicrobial agent of amikacin, gentamicin, kanamycin, neomycin, netilmicin, tobramycin, paromomycin, spectinomycin, geldanamycin, herbimycin, rifaximin, streptomycin, loracarbef, ertapenem, doripenem, imipenem, cilastatin, meropenem, cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole, teicoplanin, vancomycin, telavancin, clindamycin, lincomycin, daptomycin, azithromycin, clarithromycin, dirithromycin, erythromycin, roxithromycin, troleandomycin, telithromycin, spiramycin, aztreonam, furazolidone, nitrofurantoin, linezolid, posizolid, radezolid, torezolid, amoxicillin, ampicillin, azlocillin, carbenicillin, cloxacillin, dicloxacillin, mezlocillin, methicillin, nafcillin, oxacillin, penicillin G, penicillin V, piperacillin, penicillin G, temocillin, ticarcillin, clavulanate, sulbactam, tazobactam, bacitracin, colistin polymyxin B, ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfamethoxazole, sulfasalazine, sulfisoxazole, trimethoprim-sulfamethoxazole, sulfonamidochrysoidine, demeclocycline, doxycycline, minocycline, oxytetracycline, tetracycline, clofazimine, dapsone, capreomycin, cycloserine, ethambutol, ethionamide, isoniazid, pyrazinamide, rifampicin, rifabutin, rifapentine, streptomycin, arsphenamine, chloramphenicol, fosfomycin, fusidic acid, metronidazole, mupirocin, platensimycin, quinupristin, dalfopristin, thiamphenicol, tigecycline, tinidazole and trimethoprim.

According to other embodiments of the present disclosure, said pharmaceutical or health care composition is an antitumor composition, in which the functional cores of multilayer or porous pore-shell particles may comprise an antitumor agent. Non-limiting examples of the antitumor agent include, actinomycin, all-trans retinoic acid, alitretinoin, azacitidine, azathioprine, bevacizumab, bexarotene, Neomycin, bortezomib, carboplatin, capecitabine, cetuximab, cisplatin, chlorambucil, cyclophosphamide, cytarabine, daunorubicin, docetaxel, doxifluridine, doxorubicin, epirubicin, epothilone A-F, erlotinib, etoposide, fluorouracil, gemcitabine, gefitinib, hydroxyurea, idarubicin, imatinib, ipilimumab, irinotecan, mechlorethamine, melphalan, mercaptopurine, methotrexate, mitoxantrone, ocrelizumab, ofatumumab, oxaliplatin, paclitaxel, panitumab, pemetrexed, rituximab, romidepsin, tafluposide, teniposide, tioguanine, topotecan, tretinoin, valrubicin, vemurafenib, vinblastine, vincristine, vindesine, vinorelbine, vismodegib, and vorinostat.

In the sixth aspect, the present disclosure is directed to a method for selectively inhibiting the growth or metabolism of the cariogenic and/or periodontopathic microorganisms in a subject by using the oral care composition according to the fifth aspect and related embodiments of the present disclosure. For example, the method may selectively inhibit the growth or metabolism of cariogenic and/or periodontopathic microorganism over other nonpathogenic microorganisms existing in the oral cavity.

According to one embodiments of the present disclosure, the method comprises, administering the oral care composition according to the above-mentioned aspect/embodiments of the present disclosure to the oral cavity of the subject; and allowing the adhesion of the multilayer core-shell particles or the porous core-shell particles in the oral care composition to the oral surface of the subject.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where.

Figure 1:
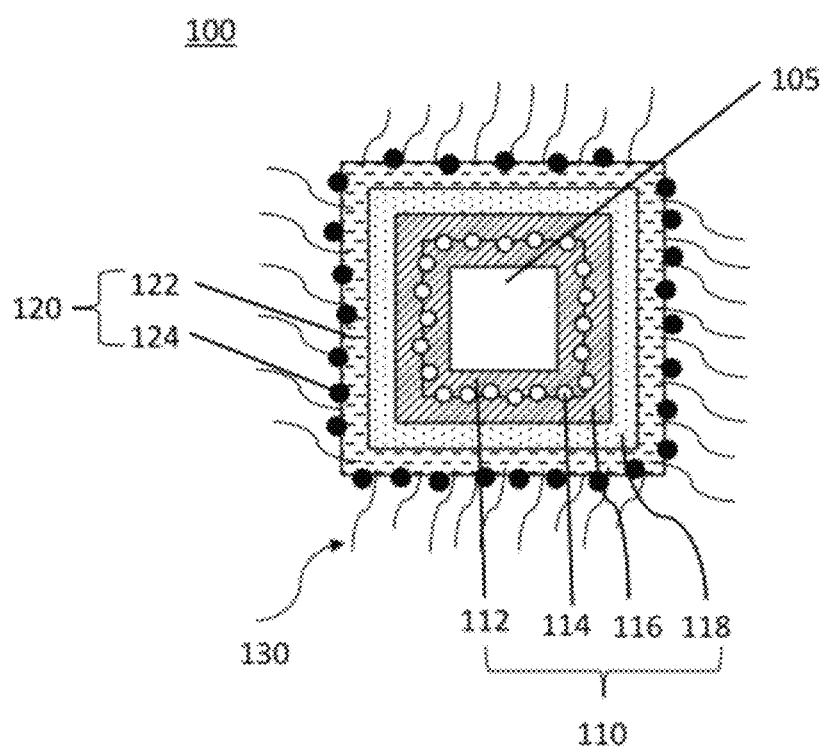
FIG. 1 is a schematic diagram illustrating a multilayer core-shell particle according to one embodiment of the present disclosure.

In accordance with common practice, the various described features/elements are not drawn to scale but instead are drawn to best illustrate specific features/elements relevant to the present invention. Also, like reference numerals and designations in the various drawings are used to indicate like elements/parts.

DETAILED DESCRIPTION OF THE INVENTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attaching claims are approximations that can vary as desired. At the very least, each numerical parameter should at least be construed in light of the number of reported significant digits and by applying ordinary rounding techniques.

As used herein, the term "active agent" refers to an agent capable of treating, inhibiting, or preventing a disorder or a disease. Exemplary active agents include, without limitation, antimicrobial agents and antitumor agents.

The term "antimicrobial agent" as used herein refers to a substance that kills one or more target microorganisms or inhibits the growth, reproduction or metabolism of the target microorganisms such as bacteria, fungi, yeast, or protozoans. Antimicrobial agents are often used to treat or prevent infections caused by the above-mentioned or other microorganisms. Accordingly, antimicrobial agents include antibiotics, antibacterial agents, antifungal agents, antiviral agents, and antiparasitic agents.

As used herein, the term "whitening agent" refers to a material that is effective in whitening a tooth surface to which it is applied.

Here, the term "antitumor agent" generically refers to a drug which acts on a variety of metabolic pathways of cancer cells and exhibits cytotoxicity or cytostatic effects on the cancer cells. Generally, the antitumor agent may include alkylating agents, anthracycline, cytoskeletal disruptors, epothilones, histone deacetylase inhibitors, topoisomerase I inhibitor, topoisomerase II inhibitor, kinase inhibitor, monoclonal antibodies, nucleotide analogs and precursor analogs, peptide antibiotics, platinum-based agents, retinoids and vinca alkaloids and derivatives.

As used herein, the term "porous" refers to a material containing pores (i.e., void regions), whether such pores are filled with another material or unfilled. The "porous ceramic shell" may have pores that are interconnected (i.e., an open cell structure) or non-interconnected (i.e., a closed cell structure), or a combination of both.

The term "pharmaceutical composition" is intended to encompass a composition comprising one or more active ingredients (such as the present core-shell particles) suitable for therapeutic use.

As used herein, the term "health care composition" is intended to mean typical materials commercially available as products or raw materials in consumer markets containing one or more active ingredients.

The term "effective amount" as referred to herein designates the quantity of a component which is sufficient to yield a desired response. For therapeutic purposes, the effective amount is also one in which any toxic or detrimental effects of the compound or composition are outweighed by the therapeutically beneficial effects. The specific effective or sufficient amount will vary with such factors as the particular condition being treated, the physical condition of the patient (e.g., the patient's body mass, age, or gender), the type of mammal or animal being treated, the duration of the treatment, the nature of concurrent therapy (if any), and the specific formulations employed and the structure of the compounds or its derivatives. Effective amount may be expressed, for example, in grams, milligrams or micrograms or as milligrams per kilogram of body weight (mg/kg).

The term "oral cavity" as used herein refers to the entire interior of the mouth, including the lips, tongue, gums, surfaces of the buccal cavity, teeth and periodontal support. Within the scope of the present disclosure, an "oral surface" includes the surfaces of the hard and soft tissues of the oral cavity.

As used herein, a "pharmaceutically acceptable excipient" is one that is suitable for use with the subjects without undue adverse side effects (such as toxicity, irritation, and allergic response) commensurate with a reasonable benefit/risk ratio. Also, each excipient must be "acceptable" in the sense of being compatible with the other ingredients of the pharmaceutical composition. The excipient can be in the form of a solid, semi-solid, or liquid diluent, cream or a capsule, As used herein, an "orally acceptable excipient" refers to a material or combination of materials that are safe for use in the oral care compositions of the present invention, without significantly degrading the efficacy of the active components of the present oral care composition. Selection of specific excipient is dependent at least on the desired product form of the present oral care composition, The term "subject" refers to a mammal including the human species that is treatable with the core-shell particles, oral care compositions and/or methods of the present invention. The term "subject" is intended to refer to both the male and female gender unless one gender is specifically indicated.

The present invention is directed to core-shell particles in which the release of the active component(s) contained in the functional core may be controlled by adjusting the shell composition or shell structure (e.g., shell thickness). According to certain embodiments of the present disclosure, the core-shell particles are pH-sensitive particles and the shell composition and/or shell structure is chosen to provide core-shell particles having faster release rate and/or higher release level of the active agent in a relatively acidic environment. This pH-dependent release property allows the design of intelligent particles that predominantly release the active component(s) in a desired environment. In certain embodiments, the shell thickness of the core-shell particles is varied so as to achieve the purpose of controlling the release rate of the active agent. According to one working example provided herein, multilayer core-shell particles having 5 shell layers (including the outermost shell layer) exhibited a sustained release of the active agent, as compared with that of core-shell particles having smaller number of shell layers.

Further, the present core-shell particles have multiple polymeric tails attaching to the outer surface thereof; these outwardly extending polymeric tails facilitate the adhesion of the present core-shell particles onto the desired target site (such as the surface of oral hard tissues like teeth enamel or bone), whereas the particles without the polymeric tails exhibited poor adhesion capability. The self-adhesive property of the present core-shell particles also results in a longer stay of the core-shell particles on the target site. According to other embodiments, the material(s) making up the polymeric tails is/are chosen so that the polymeric tails may adhere onto the soft tissues such as a tumor lesion.

Two types of core-shell particles according to embodiments of the present disclosure and processes for preparing the same are described hereinbelow in connection with drawings illustrating the schematic structure thereof.

Figure 4:
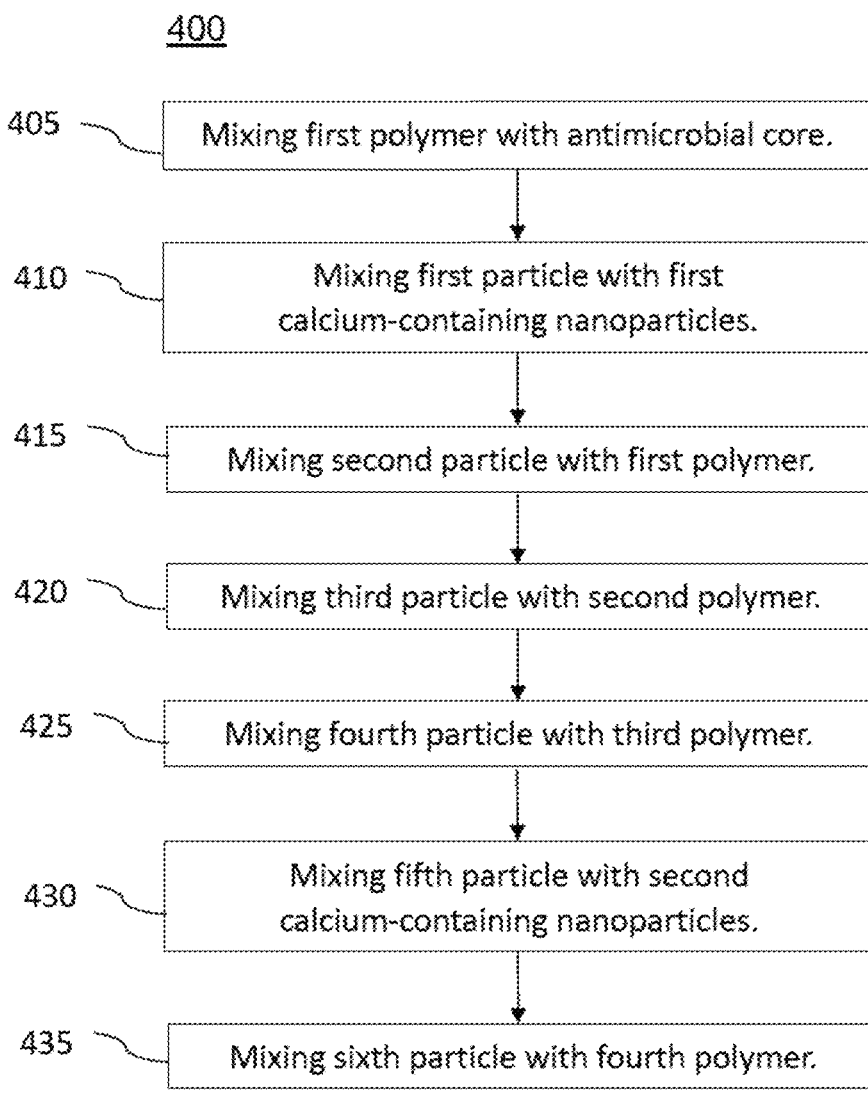
FIG. 4 is a flow chart illustrating a process for preparing a multilayer core-shell particle according to one embodiment of the present disclosure.

In one aspect, the present core-shell particle is a multilayer core-shell particle. An exemplary structure of the core-shell particle is schematically illustrated in FIG. 1, and a process for preparing the same is illustrated in FIG. 4. According to one embodiment of the present disclosure, the multilayer core-shell particle 100 comprises a functional core 105, a composite shell layer 110, an outermost shell layer 120 and a plurality of polymeric tails 130.

As illustrated in FIG. 1, the composite shell layer 110 encapsulates the outer surface of the functional core 105. Specifically, the composite shell layer 110 comprises a first polymeric layer 112, a plurality of first di- or trivalent ion-containing nanoparticles 114, a second polymeric layer 116, and a third polymeric layer 118. Structurally, the first polymeric layer 112 encapsulates the outer surface of the functional core 105, the plurality of first di- or trivalent ion-containing nanoparticles 114 adheres onto the outer surface of the first polymeric layer, the second polymeric layer covers the exposed surface of the first polymeric layer and the plurality of di- or trivalent ion-containing nanoparticles, and the third polymeric layer encapsulates the outer surface of the second polymeric layer.

The outermost shell layer 120 encapsulates the outer surface of the composite shell layer 110. Specifically, the outermost shell layer 120 comprises a fourth polymeric layer 122 encapsulating the outer surface of the composite shell layer 110 and a plurality of second di- or trivalent ion-containing nanoparticles 124 adhering onto the outer surface of the fourth polymeric layer 122.

The plurality of polymeric tails 130 attach to the outer surface of the outermost shell layer 120 and extend outwardly therefrom.

Regarding the materials forming the above-mentioned polymeric layers, both the first polymeric layer 112 and the second polymeric layer 116 are made of the same first polymer that is oppositely charged to the functional core; the third polymeric layer 118 is made of a second polymer that is oppositely charged to the first polymer, while the fourth polymeric layer 122 is made of a third polymer that has the same charge as the first polymer. The polymeric tails respectively comprise a fourth polymer that can be a cationic, anionic or neutral polymer.

FIG. 4 is a flow chart that schematically illustrates the process for preparing the multilayer core-shell particles of FIG. 1. Briefly, in steps 405 to 420, a composite shell layer 110 is formed on the outer surface of the functional core 105; next, in steps 425 to 430, an outermost shell layer 120 is formed on the outer surface of the composite shell layer 110; and then in step 435, a plurality of polymeric tails 130 are formed. Detailed process steps of process 400 are discussed below.

First, in step 405, the functional core 105 is mixed with a first polymer to form the first polymeric layer 112 that encapsulates the outer surface of the functional core 105. For example, appropriate ratio of the functional core 105 and the first polymer are mixed under stirring; then the encapsulation is allowed to proceed for a sufficient period of time before the encapsulated particles (i.e., the first particles) are collected.

Next, in step 410, appropriate amounts of the first particles and the first di- or trivalent ion-containing nanoparticles are mixed with continuous stirring, so as to allow the first di- or trivalent ion-containing nanoparticles 114 to adhere onto the respective outer surfaces of the polymeric layer 112 of the first particles, and then the resultant second particles are collected.

In step 415, the second particles are then mixed with a sufficient amount of the first polymer with continuous stirring to form a third particle, in which a second polymeric layer 116 made of the first polymer covers the exposed surface of the first di- or trivalent ion-containing nanoparticles 114 and the first polymeric layer 112 of the first particle.

Subsequently, in step 420, a suitable amount of the third particle is mixed, under stirring, with a second polymer that is oppositely charged to the first polymer. The mixture is stirred for a sufficient period of time to allow the formation of a fourth particle, in which a third polymeric layer 118 made of the second polymer encapsulates the outer surface of the second polymeric layer 116 of the third particle.

After the formation of one composite shell layer 110, which encapsulates the functional core 115, the fourth particle is subjected to step 425 and mixed with an appropriate amount of a third polymer, under stirring, to allow the formation of a fifth particle. The fifth particle has a fourth polymeric layer 122 made of the third polymer; and the fourth polymeric layer 122 encapsulates the outer surface of the third polymeric layer 118 of the fourth particle.

Thereafter, in step 430, appropriate amounts of the fifth particle and the second di- or trivalent ion-containing nanoparticles are mixed under stirring to form a sixth particle. The mixture is stirred for a sufficient period of time to allow the adhesion of the second di- or trivalent ion-containing nanoparticles 124 onto the outer surface of the fourth polymeric layer 122.

Then, in step 435, the sixth particle is mixed with a fourth polymer under stirring in an appropriate ratio so as to allow the formation of polymeric tails that respectively extend from the outer surface of the outermost shell layer 120. The resultant particles are the multilayer core-shell particles 100.

Figure 2:
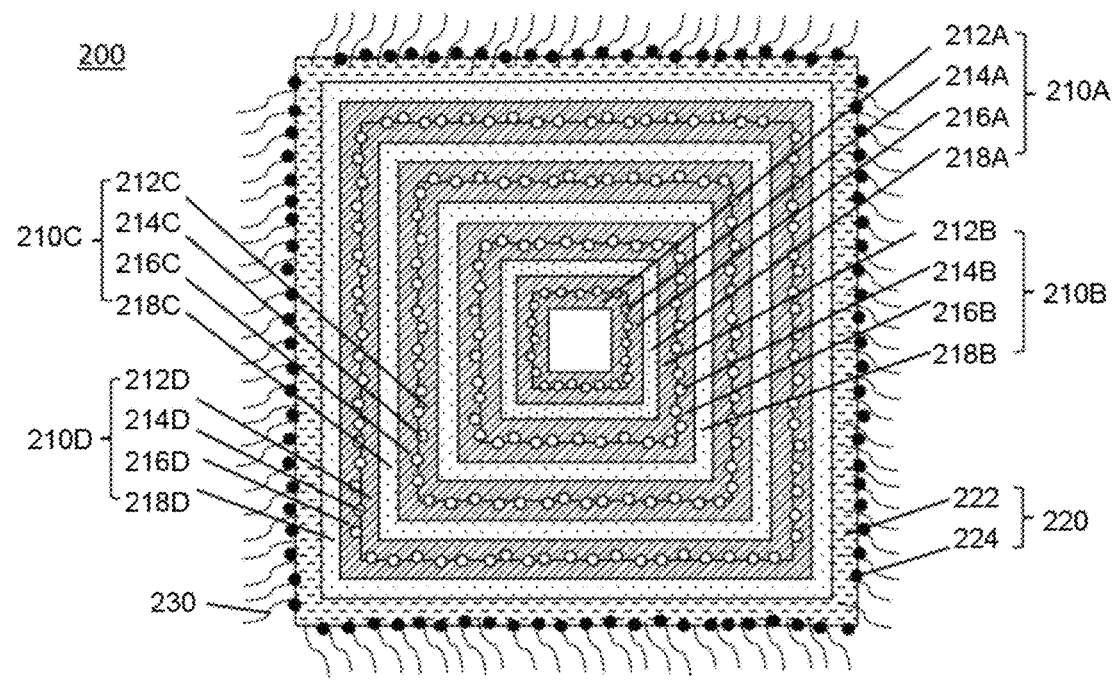
FIG. 2 is a schematic diagram illustrating a multilayer core-shell particle according to another embodiment of the present disclosure.

According to one embodiment of the present disclosure, the multilayer core-shell particle may comprise a maximum of 40 composite shell layers. For example, the multilayer core-shell particle may have 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 composite shell layers. An exemplary multilayer core-shell particle having four composite shell layers is illustrated in FIG. 2. Specifically, the multilayer core-shell particle 200 comprises a functional core 205, four composite shell layers 210A, 210B, 210C and 210D, an outermost shell layer 220 and a plurality of polymeric tails 230. The compositions and arrangement of the functional core 205, the outermost shell layer 220 and plurality of polymeric tails 230 are respectively similar to those disclosed above in connection with FIG. 1, and hence, detailed description thereof is omitted herein for the sake of brevity.

Each of the four composite shell layers 210A, 210B, 210C and 210D comprises a first polymeric layer (212A, 212B, 212C or 212D), a plurality of first di- or trivalent ion-containing nanoparticles (214A, 214B, 214C or 214D), a second polymeric layer (2146, 216B, 216C or 216D), and a third polymeric layer (218A, 218B, 218C or 2148). The structural relationship among these constituting components is the same as that described above in connection with FIG. 1, and hence, detailed description thereof is omitted herein for the sake of brevity.

For the preparation of the multilayer core-shell particles having more than one composite shell layers, the steps 405 to 420 are sequentially repeated for a desired number of times before the step 425 is performed. For example, to prepare the multilayer core-shell particles 200, a first round of steps 405 to 420 are performed to form the first composite shell layer 210A encapsulating the functional core 205; then a second, third and fourth rounds of steps 405 to 420 are performed, thereby sequentially forming the second composite shell layer 210B, the third composite shell layer 210C and the fourth composite shell layer 210D. Then, steps 425 to 435 are performed to produce the outermost layer 220 (including the fourth polymeric layer 222 and second di- or trivalent ion-containing particles 224) and the polymeric tails 230.

According to various embodiments of the present disclosure, the functional core 105, 205 comprises an antimicrobial agent of sodium fluoride, calcium fluoride, acidulated phosphate fluoride, stannous fluoride, triclosan, chlorhexidine, amikacin, gentamicin, kanamycin, neomycin, netilmicin, tobramycin, paromomycin, spectinomycin, geldanamycin, herbimycin, rifaximin, streptomycin, loracarbef, ertapenem, doripenem, imipenem, cilastatin, meropenem, cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole, teicoplanin, vancomycin, telavancin, clindamycin, lincomycin, daptomycin, azithromycin, clarithromycin, dirithromycin, erythromycin, roxithromycin, troleandomycin, telithromycin, spiramycin, aztreonam, furazolidone, nitrofurantoin, linezolid, posizolid, radezolid, torezolid, amoxicillin, ampicillin, azlocillin, carbenicillin, cloxacillin, dicloxacillin, mezlocillin, methicillin, nafcillin, oxacillin, penicillin G, penicillin V, piperacillin, penicillin G, temocillin, ticarcillin, clavulanate, sulbactam, tazobactam, bacitracin, colistin polymyxin B, ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfamethoxazole, sulfanilamide, sulfasalazine, sulfisoxazole, trimethoprim-sulfamethoxazole, sulfonamidochrysoidine, demeclocycline, doxycycline, minocycline, oxytetracycline, tetracycline, clofazimine, dapsone, capreomycin, cycloserine, ethambutol, ethionamide, isoniazid, pyrazinamide, rifampicin, rifabutin, rifapentine, streptomycin, arsphenamine, chloramphenicol, fosfomycin, fusidic acid, metronidazole, mupirocin, platensimycin, quinupristin, dalfopristin, thiamphenicol, tigecycline, tinidazole and trimethoprim.

In certain embodiments of the present disclosure, the functional core 105, 205 may comprise a whitening agent, such as hydrogen peroxide, carbamide peroxide, and zinc oxide. It should be noted that, although these compounds are listed as "whitening agent" here, they may exhibit other functions other than whitening. For example, it is well known that hydrogen peroxide, carbamide peroxide, and zinc oxide are also effective as antimicrobial agent. Accordingly, in some preferred embodiments of the present disclosure, it is advantageous to include these dual- or multi-effect agents in an oral care composition for they can act as an antimicrobial agent and a whitening agent at the same time. Alternatively, in certain embodiments of the present disclosure, the functional core may comprise both the antimicrobial agent (e.g., sodium fluoride) and the whitening agent (e.g., zinc oxide.)

According to some other embodiments, the functional core 105, 205 comprises an active agent which is an antitumor agent. Non-limiting examples antitumor agents suitable for use herein are (1) alkylating agents, including, cyclophosphamide, mechlorethamine, chlorambucil, and melphalan; (2) anthracycline, including, daunorubicin, doxorubicin, epirubicin, idarubicin, mitoxantrone and valrubicin; (3) cytoskeletal disruptors, including, paclitaxel and docetaxel; (4) epothilones, including, epothilone A to F; (5) histone deacetylase inhibitors, including, vorinostat and romidepsin; (6) topoisomerase I inhibitor, including, irinotecan and topotecan; (7) topoisomerase II inhibitor, including, etoposide, teniposide, and tafluposide; (8) kinase inhibitor, including, bortezomib, erlotinib, gefitinib, imatinib, vemurafenib and vismodegib; (9) monoclonal antibodies, including, bevacizumab, cetuximab, ipilimumab, ofatumumab, ocrelizumab, panitumab and rituximab; (10) nucleotide analogs and precursor analogs, including, azacitidine, azathioprine, capecitabine, cytarabine, doxifluridine, fluorouracil, gemcitabine, hydroxyurea, mercaptopurine, methotrexate, and tioguanine; (11) peptide antibiotics, including, Neomycin and actinomycin; (12) platinum-based agents, including, carboplatin, cisplatin and oxaliplatin; (13) retinoids, including, tretinoin, alitretinoin and bexarotene; and (14) vinca alkaloids and derivatives, including, vinblastine, vincristine, vindesine vinorelbine, and vorinostat.

According to embodiments of the present disclosure, the first di- or trivalent ion-containing nanoparticles 114, 214 or the second di- or trivalent ion-containing nanoparticles 124, 224 comprise a material selected from the group consisting of hydroxyapatite, fluoroapatite, calcium phosphate, calcium fluoride, zinc oxide, silicate, titanium oxide and a combination thereof. In various embodiments of the present disclosure, the first di- or trivalent ion-containing nanoparticles 114, 214 and the second di- or trivalent ion-containing nanoparticles 124, 224 could be the same or different particle. As could be appreciated, hydroxyapatite reacts with most fluoride-containing materials to form fluoroapatite and calcium fluoride. Therefore, in the embodiments where the functional core 105, 205 comprises a fluoride-based agent (e.g., sodium fluoride), the hydroxyapatite in the first di- or trivalent ion-containing nanoparticle 114, 214 and/or second di- or trivalent ion-containing nanoparticles 124, 224 may react with the fluoride released from the functional core 105, 205, and thereby forms a hydroxyapatite/fluoroapatite/calcium fluoride composite nanoparticle. Alternatively, the first di- or trivalent ion-containing nanoparticle 114, 214 or the second di- or trivalent ion-containing nanoparticles 124, 224 may be pre-made composite nanoparticles comprising a combination of at least two of hydroxyapatite, fluoroapatite, calcium phosphate and calcium fluoride.

According to certain embodiments of the present disclosure, at least one of the first, second and third polymers is a cationic polymer. A common cationic polymer often presents free amino groups that are positively charged. Non-limiting examples of cationic polymers include polyarginine, polylysine, polyhistidine, poly-ornithine, polyethyleneimine, polypropyleneimine, poly(allylamine), polystyrene-maleic acid, gelatin and chitosan.

In some embodiments of the present disclosure, at least one of the first, second and third polymers is an anionic polymer. Most anionic polymers present negatively-charged free carboxylic groups, examples of which include, but are not limited to, polyacrylic acid, polymethacrylic acid, polycrotonic acid, polyaspartic acid, polyglutamic acid, polylactic acid, polylactic-co-glycolic) acid, hyaluronic acid, alginic acid, polystyrene sulfonate, carrageenan, poly (methylene-co-guanidine), polyphosphoric acid, and pamidronic acid.

According to embodiments of the present disclosure, the fourth polymer suitable for forming the polymeric tails may be a cationic, anionic or neutral polymer. Non-limiting examples of polymers suitable for use herein include, polyarginine, polylysine, polyhistidine, poly-ornithine, polyethyleneimine, polypropyleneimine, poly(allylamine), polystyrene-maleic acid, gelatin, chitosan, polyacrylic acid, polymethacrylic acid, polycrotonic acid, polyaspartic acid, polyglutamic acid, polylactic acid, poly(lactic-co-glycolic) acid, hyaluronic acid, and alginic acid, polystyrene sulfonate, carrageenan, poly(methylene-co-guanidine), polyphosphoric acid, or pamidronic acid, xanthan gum, polycarbophil, poly(methylvinyl ether-co-maleic anhydride), shellac, agar, pectin, polyvinyl acetate phthalate, guar gum, polyethylene glycol, dextrin, polydextrose, and polyethylene oxide.

As could be appreciated, the first and third polymers have the same charge, and hence, in certain embodiments of the present disclosure, the first and third polymers are the same polymer; however, the present invention is not limited thereto, and the first and third polymers may be different polymers, In certain embodiments of the present disclosure, the thickness of the one or more composite shell layers and the outermost shell is about 0.5 to 1,000 nm. For example, the total thickness may be 0.5, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 100, 150, 200, 250, 300, 350, 400, 450, 500, 550, 600, 650, 700, 750, 800, 850, 900, 950, or 1,000 nm. Generally, the total thickness of the composite shell layer(s) and the outermost shell depends on the respective thickness of each polymeric layer thereof, and the number of composite shell layers.

According to some embodiments of the present disclosure, the average diameter of the multilayer core-shell particle is about 50 to 50,000 nm. For example, the average diameter may be 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000, 5000, 5500, 6000, 6500, 7000, 7500, 8000, 8500, 9000, 9500, 10000, 15000, 20000, 25000, 30000, 35000, 40000, 45000, or 50000 nm, Although the multilayer core-shell particles 100 and 200 illustrated in FIG. 1 and FIG. 2 are cubic particles, the present invention is not limited thereto. Rather, the multilayer core-shell particles according to various embodiments of the present disclosure may have other shapes, such as, needle, spherical, pyramidal or polygonal cylindrical.

As could be appreciated, for a core-shell particle, the shape of the final particle is often largely depends on the crystal shape of the material(s) forming the core. However, for a multilayered core-shell particle, such as the instantly claimed one, it is often difficult to maintain the original shape of the core during the repetitive layer-forming steps. Nonetheless, as is evident from the working examples provided hereinbelow, the preparation process according to embodiments of the present disclosure would not result in the loss of fidelity of the crystal shape of the active agent.

In some embodiments of the present disclosure, the multilayer core-shell particles are pH-sensitive particles tend to release the active agent therefrom in a pH-dependent manner. Specifically, the multilayer core-shell particles according to the working examples of the present disclosure release higher level of the active agent in lower pH. Also, these multilayer core-shell particles exhibit a faster release rate in a more acidic environment.

According to embodiments of the present disclosure, the functional core comprises sodium fluoride; the first, third and fourth polymers are polyacrylic acid; the second polymer is polyethyleneimine; the first and second di- or trivalent ion-containing nanoparticles are composite nanoparticles made of hydroxyapatite, fluoroapatite and calcium fluoride; and the multilayer core-shell particles have 4 to 10 composite shell layers.

Figure 3:
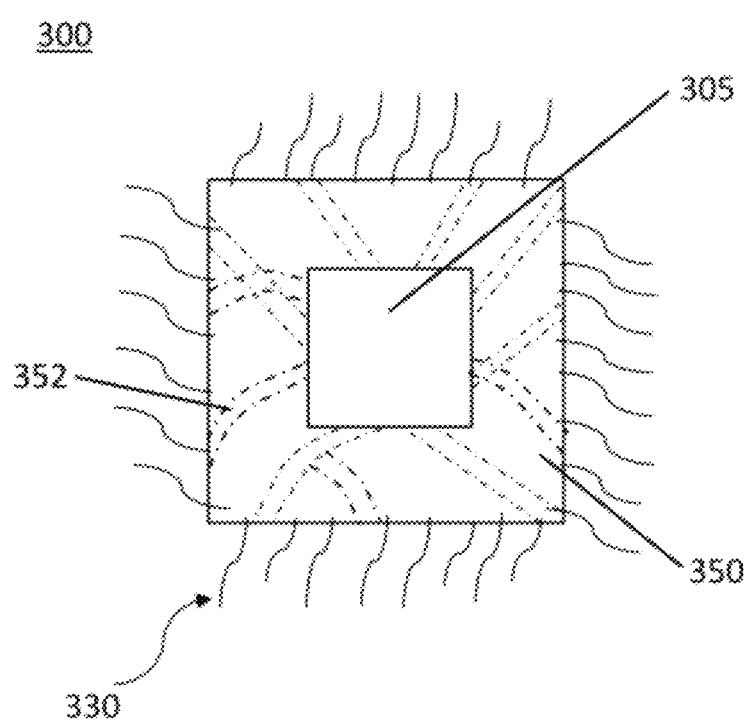
FIG. 3 is a schematic diagram illustrating a porous core-shell particle according to yet another embodiment of the present disclosure.
Figure 5:
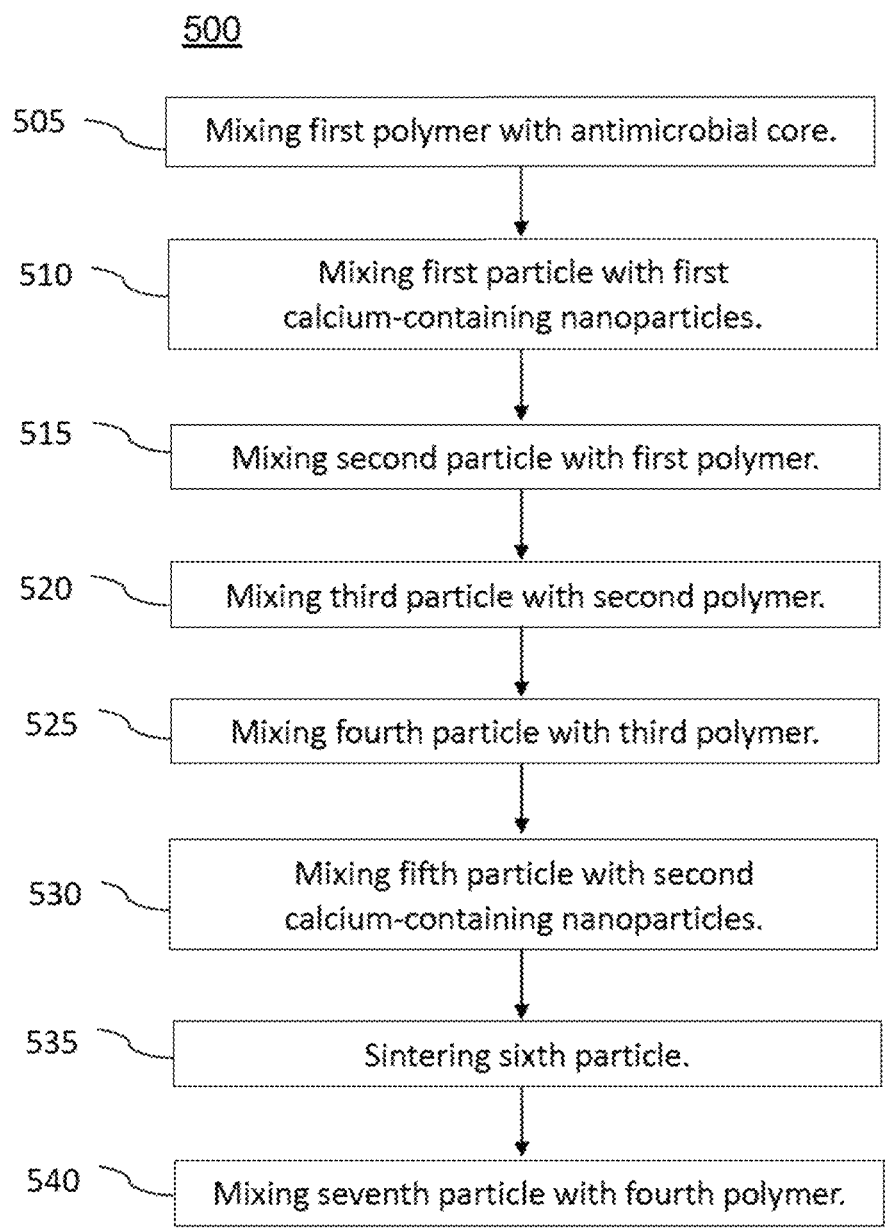
FIG. 5 is a flow chart illustrating a process for preparing a porous core-shell particle according to another embodiment of the present disclosure.

In another aspect, the core-shell particle according to the present disclosure is a porous core-shell particle, which is schematically illustrated in FIG. 3, and a process for preparing the same is illustrated in FIG. 5. According to one embodiment of the present disclosure, the porous core-shell particle 300 comprises a functional core 305, a porous ceramic shell 350, and a plurality of polymeric tails 330.

As illustrated in FIG. 3, the porous ceramic shell 350 encapsulates the outer surface of the functional core 305. The porous ceramic shell 350 has a plurality of pores (or voids) 352 formed across the ceramic matrix. Some of these pores 352 may be connected to another pore 352; while some pores 352 are not connected to any other pores. Further, some pores 352 may form a channel open at the outer surface of the porous ceramic shell 350.

Each of the plurality of polymeric tails 130 attaches to the outer surface of the porous ceramic shell 350 and extends outwardly therefrom. The polymeric tails may comprise a cationic, anionic or neutral polymer, as discussed above.

FIG. 5 is a flow chart that schematically illustrates the process for preparing the porous core-shell particles of FIG. 3. In sum, the preparation process 500 is quite similar to the preparation process 400 discussed above, except that before the formation of polymeric tails, the particle is subject to a sintering step so as to form the porous ceramic shell.

Specifically, process steps 505 to 530 are performed to sequentially form the composite shell layer and the outermost layer encapsulating the functional core 305. As could be appreciated, steps 505 to 530 are respectively the same as steps 405 to 430 discussed hereinabove, and hence, detailed description thereof is omitted herein for the sake of brevity. Also, it should be noted that process steps 505 to 515 may be repeated for a desired number of times before the steps 520 and 530 are performed.

The sixth particle produced from step 530 are collected and then a sintering step is performed so that the first and second di- or trivalent ion-containing nanoparticles are sintered to form a ceramic matrix, while the first and second polymer of the first, second and third polymeric layers are evaporated as a result of the high sintering temperature. As could be noted, during the evaporation, the vapor of the polymers pass through the ceramic matrix being formed, thereby leaving pores (voids) in the ceramic matrix. In this way, a porous ceramic matrix 350 is formed around the functional core 305, thereby producing a seventh particle.

The sintering condition generally depends on the composition of the first and second di- or trivalent ion-containing nanoparticles, the composite shell layer(s) and/or the outermost layers, as well as the total thickness of these layers. According to various embodiments of the present disclosure, a sintering condition comprising a sintering temperature of about 200° C. to 800° C. and a sintering time of about 1 to 10 hours is sufficient to produce the porous ceramic shell. For example, the sintering temperature may be about 200, 250, 300, 350, 400, 450, 500, 550, 600, 650, 700, 750, or 800° C., while the sintering time may be about 1, 1.5, 2, 2.5, 3, 3.5, 4, 4.5, 5, 5.5, 6, 6.5, 7, 7.5, 8, 8.5, 9, 9.5, or 10 hours.

Then in step 535, polymeric tails 330 respectively attaching to and extending outwardly from the outer surface of the porous ceramic matrix 350 are formed by mixing the seventh particles with a fourth polymer.

As discussed above, the matrix of the porous ceramic shell 530 is made of the first and second di- or trivalent ion-containing nanoparticles, and hence, the porous ceramic shell is made of the same material as the first and second di- or trivalent ion-containing nanoparticles. For example, the porous ceramic shell 530 is made of hydroxyapatite, fluoroapatite, calcium phosphate, calcium fluoride, zinc oxide, silicate, titanium oxide or a combination thereof.

The antimicrobial and the first, second, third and fourth polymers discussed hereinabove in connection with the preparation process 400 are equally applicable in the preparation process 500. Accordingly, a detailed description regarding these materials is omitted herein for the sake of brevity.

In certain embodiments of the present disclosure, the porous ceramic shell 350 has a thickness of about 0.5 to 1,000 nm; such as, 0.5, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 100, 150, 200, 250, 300, 350, 400, 450, 500, 550, 600, 650, 700, 750, 800, 850, 900, 950, or 1,000 nm.

According to some embodiments of the present disclosure, the average diameter of the porous core-shell particle 300 is about 50 to 5000 nm; e.g., 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500 or 50,000 nm.

Although the porous core-shell particle 300 depicted in FIG. 3 is a cubic particle, the present invention is not limited thereto. Rather, the porous core-shell particles according to various embodiments of the present disclosure may be a needle-like, spherical, pyramidal or polygonal cylindrical particle.

Similar to the multilayer core-shell particles described above, the porous core-shell particles according to certain embodiments of the present disclosure are also pH-dependent particles. Accordingly, these porous core-shell particles, when being put in a more acidic environment, tend to release more active agents therein in a faster manner.

The present disclosure also comprises pharmaceutical or health care compositions for administration or application to, or use with, a human or other animal subject. The present pharmaceutical or health care compositions comprise any of the core-shell particles according to aspects/embodiments of the present disclosure.

According to embodiments of the present disclosure, the pharmaceutical or health care composition comprises an effective amount of the multilayer core-shell particles described hereinabove, and a pharmaceutically acceptable excipient.

According to other embodiments of the present disclosure, the pharmaceutical or health care composition comprises an effective amount of the porous core-shell particles described hereinabove, and a pharmaceutically acceptable excipient.

The pharmaceutical or health care composition is prepared in accordance with acceptable, established pharmaceutical procedures. The choice of a pharmaceutically acceptable excipient to be used in conjunction with the present core-shell particles is basically determined by the desired product form of the pharmaceutical or health care composition.

The pharmaceutical or health care composition according to the present disclosure may be administered by any suitable route, for example, by oral, parenteral (such as intramuscular, intravenous, subcutaneous, or intraperitoneal injection), topical or transmucosal administration.

For oral administration, the present core-shell particles may be formulated into tablets containing various excipients such as microcrystalline cellulose, sodium citrate, calcium carbonate, dicalcium phosphate, and glycine; along with various disintegrants such as starch, alginic acid and certain silicates; together with granulation binders like polyvinylpyrrolidone, sucrose, gelatin and acacia. Additionally, lubricating agents such as magnesium stearate, sodium lauryl sulfate and talc may be added. Solid composition may also be employed as fillers in gelatin capsules; preferred materials in this connection also include lactose or milk sugar as well as high molecular weight polyethylene glycols. When aqueous suspensions and/or elixirs are desired for oral administration, the present core-shell particles may be combined with various sweetening or flavoring agents, coloring matter or dyes, and if so desired, emulsifying and/or suspending agents as well, together with diluents such as water, ethanol, propylene glycol, glycerin and a combination thereof.

For parenteral administration, the present core-shell particles may be formulated into liquid pharmaceutical compositions, which are sterile solutions, or suspensions that can be administered by, for example, intravenous, intramuscular, subcutaneous, or intraperitoneal injection. Suitable diluents or solvent for manufacturing sterile injectable solution or suspension include, but are not limited to, 1,3-butanediol, mannitol, water, Ringer's solution, and isotonic sodium chloride solution, Fatty acids, such as oleic acid and its glyceride derivatives are also useful for preparing injectables, as are natural pharmaceutically-acceptable oils, such as olive oil or castor oil. These oil solutions or suspensions may also contain alcohol diluent or carboxymethyl cellulose or similar dispersing agents. Other commonly used surfactants such as Tweens or Spans or other similar emulsifying agents or bioavailability enhancers that are commonly used in manufacturing pharmaceutically acceptable dosage forms can also be used for the purpose of formulation.

For topical administration, the present core-shell particles may be formulated into a variety of dosage forms for topical application. A wide variety of dermatologically acceptable inert excipients well known to the art may be employed. The topical compositions may include liquids, creams, lotions, ointments, gels, sprays, aerosols, skin patches, and the like. Typical inert excipients may be, for example, water, ethyl alcohol, polyvinyl pyrrolidone, propylene glycol, mineral oil, stearyl alcohol and gel-producing substances. All of the above dosages forms and excipients are well known to the pharmaceutical art. The choice of the dosage form is not critical to the efficacy of the composition described herein.

For transmucosal administration, the present core-shell particles may also be formulated in a variety of dosage forms for mucosal application, such as buccal and/or sublingual drug dosage units for drug delivery through oral mucosal membranes. A wide variety of biodegradable polymeric excipients may be used that are pharmaceutically acceptable, provide both a suitable degree of adhesion and the desired drug release profile, and are compatible with the active agents to be administered and any other components that may be present in the buccal and/or sublingual drug dosage units. Generally, the polymeric excipient comprises hydrophilic polymers that adhere to the wet surface of the oral mucosa. Examples of polymeric excipients include, but are not limited to, acrylic acid polymers and copolymers; hydrolyzed polyvinylalcohol; polyethylene oxides; polyacrylates; vinyl polymers and copolymers; polyvinylpyrrolidone; dextran; guar gum; pectins; starches; and cellulosic polymers.

As a non-limiting example, the pharmaceutical or health care composition is an oral care composition that is suitable for administration to the oral cavity a human or animal subject for enhancing the health, hygiene or appearance of the subject. As could be appreciated, the food digestion and metabolites of cariogenic microorganisms often result in a more acidic environment in the oral cavity. However, the multilayer core-shell particles or the porous core-shell particles can be devised to be a pH-dependent release system, and hence, the acidic environment may trigger the release of the active agents contained in the core-shell particles. In one example, the release rate of the active agent is higher when the core-shell particle is in a relatively acidic environment. Alternatively or additionally, the total release amount of the active agent is higher when the core-shell particle is in a relatively acidic environment. As such, the present oral care composition may selectively inhibit the growth or metabolism of cariogenic and/or periodontopathic microorganisms. To the contrary, when the oral cavity is in a neutral or alkaline environment with a pH value of 7.0 or above; relatively fewer amounts of the active agents would be released from the oral care composition. In this way, the probiotic microorganisms in the oral cavity are retained, thereby maintain the ecosystem of oral biota.

Further, the adhesive nature of the polymeric tails of the present core-shell particles promotes the staying time of the core-shell particles in the oral cavity for the self-adhesiveness can act against the washing-off by food digestion and/or saliva secretion. Moreover, the core layer(s) of the present core-shell particles comprise di- or trivalent ion-containing materials that promote remineralization of the hard tissues such as enamel of the tooth.

According to certain embodiments of the present disclosure, the oral care composition may comprise a plurality of multilayer or porous core-shell particles in which the functional core thereof comprises an antimicrobial agent. For example, the antimicrobial agent can be sodium fluoride, calcium fluoride, acidulated phosphate fluoride, stannous fluoride, triclosan, or chlorhexidine.

According to other embodiments of the present disclosure, the oral care composition may comprise a plurality of multilayer or porous core-shell particles in which the functional core thereof comprises a whitening agent, such as, hydrogen peroxide, carbamide peroxide, and zinc oxide.

In some optional embodiments, the oral care composition may comprise a plurality of multilayer or porous core-shell particles in which the functional core thereof comprises an antimicrobial agent and a whitening agent.

Still optionally, the oral care composition may comprise a first plurality of multilayer or porous core-shell particles in which the functional core thereof comprises an antimicrobial agent, and a second plurality of multilayer or porous core-shell particles in which the functional core thereof comprises a whitening agent, In various embodiments, said oral care composition is not intentionally swallowed; rather, the oral care composition or active components thereof must be retained in the oral cavity for a sufficient time to solicit the intended effect.

According to various embodiments of the present disclosure, the oral care composition can be formulated into mouthrinses, tooth cleaning compositions, confectionery compositions, or dental filling compositions.

Mouthrinses are often aqueous or suspension compositions such as a mouthwash, spray, or rinse. Tooth cleaning compositions include toothpowders, dental tablets, toothpastes or tooth gels that are intended for cleaning the hard surface of the oral cavity. Confectionery compositions, as used herein, include chewing gum and orally soluble tablets, beads, lozenges, and films. Dental filling compositions include dental cements and dental fillings.

Orally acceptable excipients for preparing any of the above-mentioned compositions include, but are not limited, water, ethanol, isopropanol, polyhydric alcohol (such as mannitol, xylitol, sorbitol, and malitol), glycerin, propylene glycol, sorbitol, polypropylene glycol, and polyethylene glycol.

In addition to the orally acceptable excipients, the oral composition may optionally comprise one or more additives, including, but not limited to, humectants, thickeners, surfactants, flavoring agents, sweeteners, colorants, emulsifiers, pH modifying agents, mouth-feel agents, foam modulators, and abrasives. Examples of these additives are well known in the art, and hence, detailed description regarding the same is omitted herein for the sake of brevity.

In some embodiments of the present disclosure, the pharmaceutical or health care composition is an antimicrobial composition for treating infections. In this case, the functional core of the present multilayer or porous core-shell particle may comprise one or more antimicrobial agents. For example, the antimicrobial agents can be any of amikacin, gentamicin, kanamycin, neomycin, netilmicin, tobramycin, paromomycin, spectinomycin, geldanamycin, herbimycin, rifaximin, streptomycin, loracarbef, ertapenem, doripenem, imipenem, cilastatin, meropenem, cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole, teicoplanin, vancomycin, telavancin, clindamycin, lincomycin, daptomycin, azithromycin, clarithromycin, dirithromycin, erythromycin, roxithromycin, troleandomycin, telithromycin, spiramycin, aztreonam, furazolidone, nitrofurantoin, linezolid, posizolid, radezolid, torezolid, amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, penicillin G, temocillin, ticarcillin, clavulanate, sulbactam, tazobactam, bacitracin, colistin polymyxin B, ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfamethoxazole, sulfanilimide, sulfasalazine, sulfisoxazole, trimethoprim-sulfamethoxazole, sulfonamidochrysoidine, demeclocycline, doxycycline, minocycline, oxytetracycline, tetracycline, clofazimine, dapsone, capreomycin, cycloserine, ethambutol, ethionamide, isoniazid, pyrazinamide, rifampicin, rifabutin, rifapentine, streptomycin, arsphenamine, chloramphenicol, fosfomycin, fusidic acid, metronidazole, mupirocin, platensimycin, quinupristin, dalfopristin, thiamphenicol, tigecycline, tinidazole or trimethoprim.

According to certain embodiments of the present disclosure, the pharmaceutical or health care composition is an antitumor composition that is useful in treating cancer/tumor. For an antitumor composition according to embodiments of the present disclosure, the functional core of the multilayer or porous core-shell particle comprises at least one antitumor agent capable of inhibiting or preventing tumor growth or function, and/or causing destruction of tumor cells. Exemplary antitumor agents suitable for use herein include actinomycin, all-trans retinoic acid, alitretinoin, azacitidine, azathioprine, bevacizumab, bexarotene, bleomycin, bortezomib, carboplatin, capecitabine, cetuximab, cisplatin, chlorambucil, cyclophosphamide, cytarabine, daunorubicin, docetaxel, doxifluridine, doxorubicin, epirubicin, epothilone A-F, erlotinib, etoposide, fluorouracil, gemcitabine, gefitinib, hydroxyurea, idarubicin, imatinib, ipilimumab, irinotecan, mechlorethamine, melphalan, mercaptopurine, methotrexate, mitoxantrone, ocrelizumab, ofatumumab, oxaliplatin, paclitaxel, panitumab, pemetrexed, rituximab, romidepsin, tafluposide, teniposide, tioguanine, topotecan, tretinoin, valrubicin, vemurafenib, vinblastine, vincristine, vindesine, vinorelbine, vismodegib, and vorinostat.

In another aspect, the present disclosure is directed to a method for selectively inhibiting the growth or metabolism of cariogenic and/or periodontopathic microorganisms in a subject. In the context of the present disclosure, the concept of "selective inhibition" refers to a condition in which the growth inhibition or metabolic inhibition of the cariogenic or periodontopathic microorganisms is more profound than that of non-cariogenic or non-periodontopathic microorganisms. Also in the context of the present disclosure is that the present method/oral care composition may selectively exert more inhibition effect in a condition where the metabolism of the cariogenic or periodontopathic microorganisms is more active.

According to embodiments of the present disclosure, the method comprises administering the present oral care composition to the oral cavity of the subject; and allowing the adhesion of the core-shell particles to the oral surface of the subject.

As could be appreciated, the core-shell particles according to embodiments of the present disclosure may actively adhere onto the surface of the hard tissues of the oral cavity. Hence, the method may include poring or drawing the oral composition into the mouth, and then holding the oral composition in the mouth for a period of time before spitting out, washing off or swallowing the oral composition. Alternatively, the method may include smearing or otherwise applying the oral composition over the surface of the target site (e.g., the hard tissue) with a suitable tool (such as a brush, stick, or spatula), leaving the oral composition to stay on the target site for a period of time, and then optionally washing off the oral composition. Generally, the oral composition is allowed to stay in or contact with the oral cavity for a short period of time, such as a few seconds to less than one minute, while in other cases, said period could be longer and lasts for minutes, hours, or even days.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLES

Example 1

Preparation of Multilayer Core-Shell Particles

Figure 6:
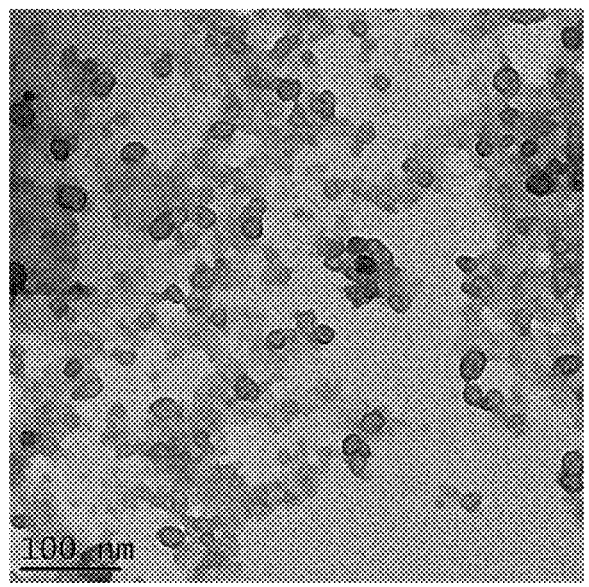
FIG. 6 is a transmission electron microscopy (TEM) image of the di- or trivalent ion-containing nanoparticles according to one embodiment of the present disclosure.

To prepare hydroxyapatite (HA) nanoparticles, 0.555 gram of calcium chloride ($CaCl_2$), 0.150 gram of sodium dihydrogen phosphate ($NaH_2PO_4$) and 0.073 gram of sodium bicarbonate ($NaHCO_3$) were dissolved in 500 mL deionized water; the solution was then allowed to react under 37° C. with a rotator (80 rpm) for 24 hours. Next, the HA nanoparticles were centrifuged at 12,000 rpm for 5 minutes, washed with deionized water for three times and then air-dried for further use. FIG. 6 is a TEM image of the HA nanoparticles.

To prepare the multilayer core-shell particles illustrated in FIG. 1, a series of particles were synthesized pursuant to process 400 of FIG. 4.

First, saturated aqueous solution of NaF (5 mL) was slowly added into 50 mL of anhydrous alcohol under vigorous stirring (400 rpm) for 1 hour to form the functional cores.

Then, 5 mL of 1 mM polyacrylic acid (PAA; mW: 5,000 kD) was mixed with the functional cores under vigorous stirring for 2 hours to form core-PAA particles were collected by centrifugation at 12,000 rpm for 5 minutes and then washed with anhydrous alcohol for three times. (Step 405)

Next, core-PAA particles and hydroxyapatite nanoparticles were mixed in a weight ratio of 1:10 in 50% ethanol and stirred for 1 hour; and collected the core-PAA-HA particles by centrifugation at a speed of 12,000 rpm for 5 minutes, followed by anhydrous alcohol wash for three times. (Step 410)

Core-PAA-HA particles were then mixed with 5 mL of 1 mM polyacrylic acid (mW: 5,000 kD) and subjected to vigorous stirring for 2 hours. To collect core-PAA-HA-PAA particles, the reaction mixture was centrifugated at 12,000 rpm for 5 minutes and then washed with anhydrous alcohol wash for three times. (Step 415)

Subsequently, core-PAA-HA-PAA particles were mixed with 5 mL of 1 mM polyethyleneimine (PEI; mW: 1800) and vigorous stirred for 2 hours to form core-PAA-HA-PAA-PEI particles. The reaction mixture was centrifuge at 12,000 rpm for 5 minutes and then washed with anhydrous alcohol for three times. (Step 420)

The core-PAA-HA-PAA-PEI particles were than mixed with 5 mL of 1 mM polyacrylic acid (mW: 5,000 kD) under vigorous stirring for 2 hours to form core-(PAA-HA-PAA-PEI)-PAA particles, which were collected by centrifugation at 12,000 rpm for 5 minutes and then washed with anhydrous alcohol for three times. (Step 425)

Next, core-(PAA-HA-PAA-PEI)-PAA particles and hydroxyapatite nanoparticles were mixed in a weight ratio of 1:10 in 50% ethanol and stirred for 1 hour; and core-(PAA-HA-PAA-PEI)-PAA-HA particles were collected by centrifugation at 12,000 rpm for 5 minutes, followed by anhydrous alcohol wash for three times. (Step 430)

Lastly, the core-(PAA-HA-PAA-PEI)-PAA-HA particles were mixed with 5 mL of 1 mM polyacrylic acid (mW: 5,000 kD) under vigorous stirring for 2 hours to form core-(PAA-HA-PAA-PEI)-PAA-HA-PAA tail particles, which were collected by centrifugation at 12,000 rpm for 5 minutes, followed by anhydrous alcohol wash for three times. The resultant core-(PAA-HA-PAA-PEI)-PAA-HA-PAA tail particles respectively have the structure of the multilayer core-shell particle of FIG. 1. (Step 435)

Multilayer core-shell particles having 2 to 4 composite shell layers were respectively prepared by repeating steps 405 to 420 before the performance of the step 425. For example, to prepare multilayer core-shell particles 200 of FIG. 2, the core-PAA-HA-PAA-PEI particles obtained in step 420 were subjected to steps 405 to 420 for 3 more times to obtain the core-(PAA-HA-PAA-PEI)$_4$ particles; then, steps 425 to 435 were performed to form core-(PAA-HA-PAA-PEI)$_4$-PAA-HA-PAA tail particles.

Figure 7:
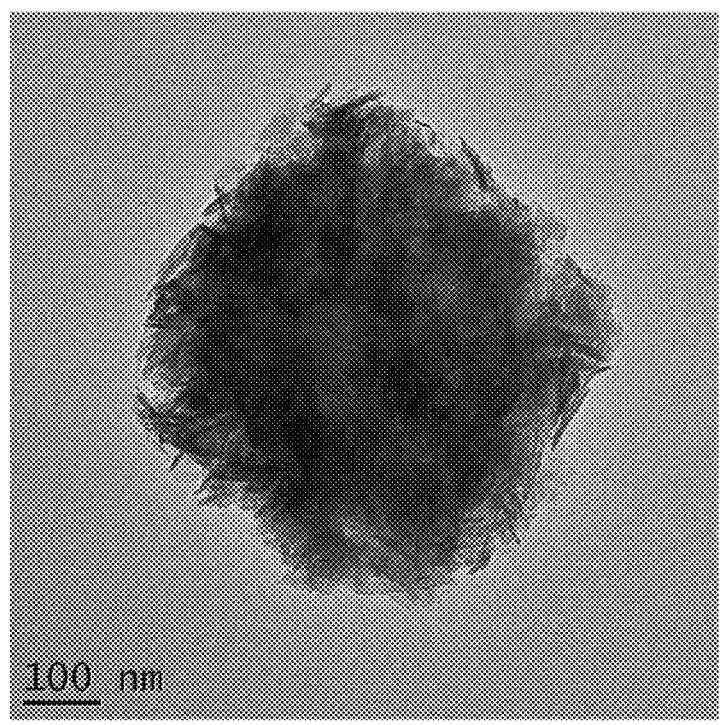
FIG. 7 is a transmission electron microscopy (TEM) image of a multilayer core-shell particle without polymeric tails.
Figure 8:
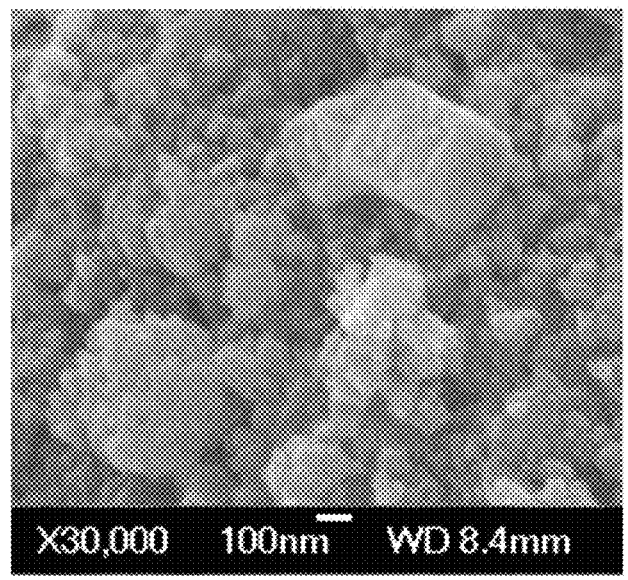
FIG. 8 is a scanning electron microscope (SEM) image of the multilayer core-shell particle of FIG. 7.

A transmission electron microscopy image and scanning electron microscopy image of the core-(PAA-HA-PAA-PEI)$_4$-PAA-HA particles are respectively provided in FIG. 7 and FIG. 8. As could be seen in FIGS. 7 and 8, the present the multilayer core-shell particles are cubic in shape.

Figure 9:
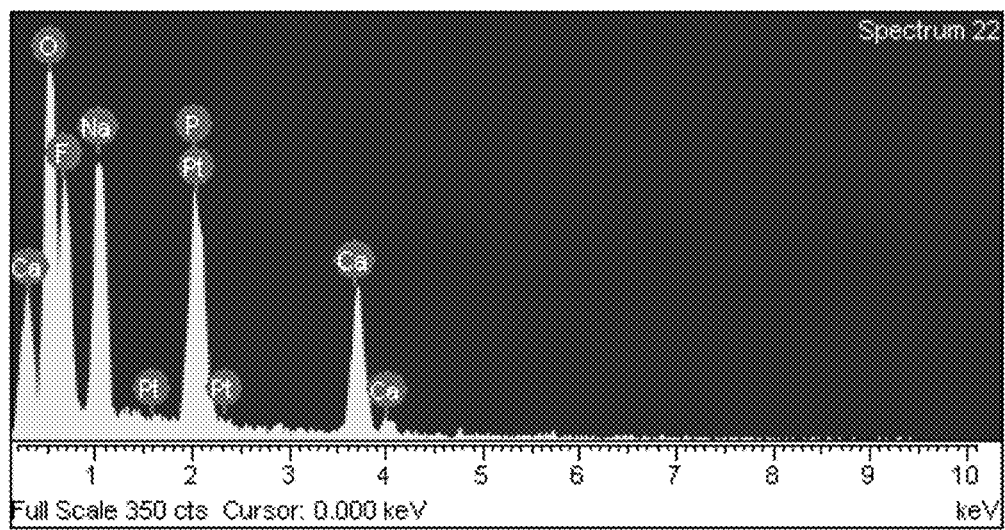
FIG. 9 is a result of energy dispersive spectrometry (EDS) of the multilayer core-shell particle of FIG. 7.

The core-(PAA-HA-PAA-PEI)$_4$ particles were also subjected to energy dispersive spectroscopic (EDS) analysis, and the results, as illustrated in FIG. 9, indicate the presence of fluoride, sodium, calcium and phosphorous signals. Accordingly, it is confirmed that the hydroxyapatite (HA) nanoparticles are present in the core-shell particles.

Figure 10:
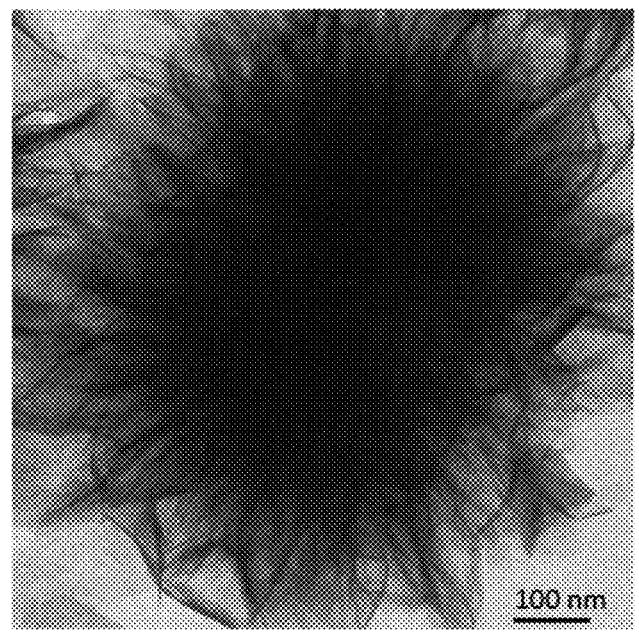
FIG. 10 is a transmission electron microscopy (TEM) image of a multilayer core-shell particle according to one embodiment of the present disclosure.

FIG. 10 is the transmission electron microscopy image of core-(PAA-HA-PAA-PEI)$_4$-PAA-HA-PAA tail particles. As could be seen in FIG. 10, the instant particle has a hair-like structure, evidencing the attachment of the PAA tails to the outermost shell layer of the particle. As could be appreciated, the lighter atoms such as carbon, hydrogen and oxygen often result in a paler color in a TEM image, while the heavier atoms such as calcium give a darker color. The dark color of the hair-like structure of the core-(PAA-HA-PAA-PEI)$_4$-PAA-HA-PAA tail particle suggests that the polymeric tails comprise calcium ions therein. The di- or trivalent ion-containing polymeric tails facilitate the adhesion of the present core-shell particles onto the hard tissues such as the enamel of the teeth.

Example 2

Preparation of Porous Core-Shell Particles

The porous core-shell particles illustrated in FIG. 3 were produced in accordance with the process 500 of FIG. 5.

Figure 11:
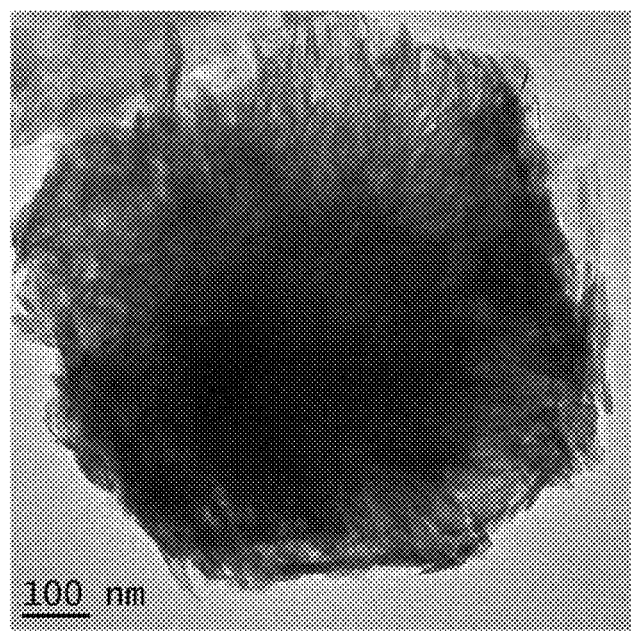
FIG. 11 is a transmission electron microscopy (TEM) image of a porous core-shell particle without polymeric tails.

Briefly, the core-(PAA-HA-PAA-PEI)$_4$ particles described in Example 1 above were sintered at 400° C. for 2 hours to form the core-porous ceramic shell particles. (Step 535). A transmission electron microscopy image of the core-porous ceramic shell particles is provided in FIG. 11.

The core-porous ceramic shell particles were then mixed with 5 mL of 1 mM polyacrylic acid (mW: 5,000 kD) under vigorous stirring for 2 hours to form core-porous ceramic shell-PAA tail particles, which were collected by centrifugation at 12,000 rpm for 5 minutes followed by anhydrous alcohol wash for three times, (Step 540)

Example 3

Adhesion of Multilayer Core-Shell Particles

The core-(PAA-HA-PAA-PEI)$_4$-PAA-HA-PAA tail particles of Example 1 were sterilized by exposing to UV light and then resuspended in sterilized deionized water to obtain a treatment solution containing 1 mg/mL multilayer core-shell particles.

Tooth extracted from a human patient was cut into slices, and smeared with the treatment solution, followed by PBS washing. SEM images in FIG. 12 indicate that the present multilayer core-shell particles adhere to the surface of the tooth enamel even after PBS washing.

For the purpose of comparison, the core-(PAA-HA-PAA-PEI)$_4$ particles without polymeric tails were also applied onto the tooth slice; however, these particles could not withstand the PBS washing (data not shown).

Example 4

Fluoride Release of Multilayer Core-Shell Particles

To evaluate the pH-dependent release of the active component(s) of the present core-shell particles, fluoride release was measured by fluoride ion electrode (Cole-Parmer Co. Cat. No. 27502-19).

First, multilayer core-shell particles having 1, 2, 3 and 4 composite shell layers as prepared in Example 1, above, were UV-sterilized and then resuspended in artificial saliva of pH 5.0 or pH 7.0 to a final concentration of 1 mg/mL, respectively. Then, the treated saliva and the total ionic strength adjuster buffer (TISAB 2) were mixed with equal volume of 1 mL, and the fluoride ion electrode was placed into said reaction solution. After the reading became stabilized, the voltage readings were recorded for 10 hours.

Figure 12:
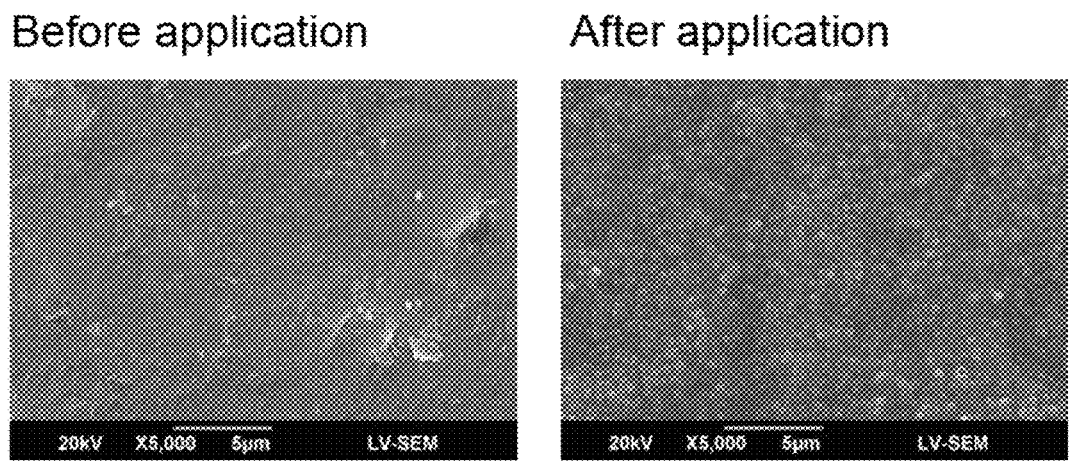
FIG. 12 includes scanning electron microscope (SEM) images of tooth enamel slice before and after the treatment with multilayer core-shell particle according to one embodiment of the present disclosure.

The results, as summarized in FIG. 12 and Table 1, indicate that in the more acid environment (i.e., artificial saliva of pH 5.0), the present multilayer core-shell particles tend to release more fluoride in a faster release manner.

TABLE 1

Fluoride Release (%) of Multilayer Core-Shell Particles

|  | pH 5 | | pH 7 | |
| --- | --- | --- | --- | --- |
|  | 0 hr | 10 hr | 0 hr | 10 hr |
| 1 composite shell layer | 47 | 91 | 14 | 36 |
| 2 composite shell layer | 45 | 69 | 6 | 20 |
| 3 composite shell layer | 16 | 37 | 7 | 13 |
| 4 composite shell layer | 11 | 25 | 6 | 12 |

For example, in the artificial saliva of pH 5.0, the fluoride release of the core-(PAA-HA-PAA-PEI)-PAA-HA-PAA tail particles reached about 47% in less than an hour, while no multilayer core-shell particles ever achieved the same level in the artificial saliva of pH 7.0 during the 10 hours of the recording period. Meanwhile, 10 hours after initiating the release, about 91% of the fluoride had been released from the core-(PAA-HA-PAA-PEI)-PAA-HA-PAA tail particles. These data establish that the present multilayer core-shell particles are pH-dependent particles that tend to release more active component contained therein in a faster fashion.

Further, by comparing the fluoride release profiles of the present multilayer core-shell particles having different numbers of composite shell layer. It is found that in the same pH environment, the multilayer core-shell particles having fewer composite shell layers release higher levels of fluoride. For example, in the artificial saliva of pH 5.0, the fluoride release levels of multilayer core-shell particles having 1, 2, 3 and 4 composite shell layers are, respectively, 91%, 69%, 37% and 25%, at the end of the 10-hour recording period.

Example 5

Antimicrobial Activity of Multilayer Core-Shell Particles

Figure 13:
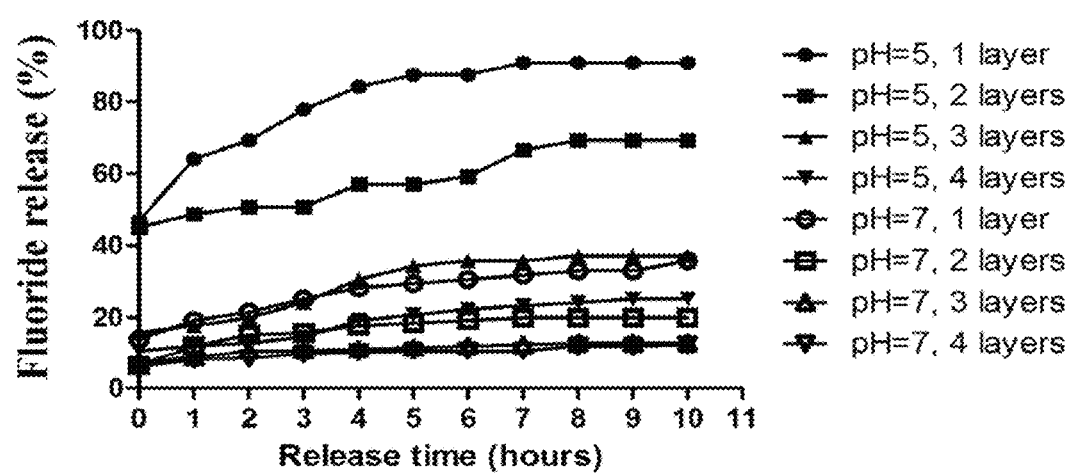
FIG. 13 is a line graph illustrating the pH-dependent release of various multilayer core-shell particles according to one embodiment of the present disclosure.
Figure 14:
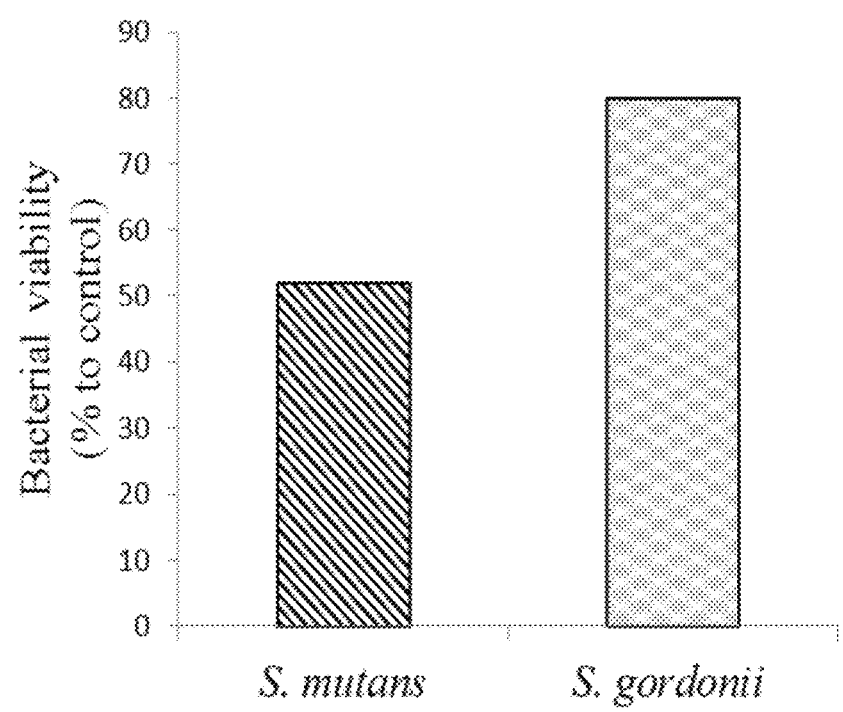
FIG. 14 is a histogram illustrating the selective inhibition of the multilayer core-shell particle according to one embodiment of the present disclosure.

Cariogenic *Streptococcus mutans* and non-cariogenic *Streptococcus gordonii* were respectively incubated at log phase and diluted at the optical density (OD 600) of 0.01 by a broth containing 1% sucrose and glucose. Then, the UV-sterilized core-(PAA-HA-PAA-PEI)$_4$-PAA-HA-PAA tail particles described above in Example 1 were added into the broth to a final concentration of 1 mg/mL, and incubated at 37° C. for 2 hours. After incubation, samples were diluted to various folds range from $10^{-4}$ to $10^{-6}$ folds. The antibacterial activity was evaluated by colony forming unit assay, and results are summarized in FIG. 13.

The viability of *S. mutans* and *S. gordonii* treated with the treatment solution were respectively about 53% and 82%, as compared with those of control un-treated bacteria. These data suggest that the present multilayer core-shell particles of Example 1 exhibit better antibacterial activity to the cariogenic *S. mutans* than to the non-cariogenic *S. gordonii*. Therefore, the present core-shell particles or oral care composition containing the same may selectively inhibit the growth or metabolism of cariogenic or periodontopathic microorganisms.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

The invention claimed is:

1. A multilayer core-shell particle, comprising,
   (a) a functional core;
   (b) one or more composite shell layers encapsulating the functional core, wherein each composite shell layer comprises,
      (b1) a first polymeric layer made of a first polymer that is oppositely charged to the functional core, wherein the first polymeric layer encapsulates the functional core,
      (b2) a plurality of first di- or trivalent ion-containing nanoparticles adhering onto the outer surface of the first polymeric layer,
      (b3) a second polymeric layer made of the first polymer, wherein the second polymeric layer covers the first polymeric layer and the plurality of di- or trivalent ion-containing nanoparticles, and
      (b4) a third polymeric layer made of a second polymer that is oppositely charged to the first polymer, wherein the third polymeric layer encapsulates the second polymeric layer;
   (c) an outermost shell layer, comprising a fourth polymeric layer and a plurality of second di- or trivalent ion-containing nanoparticles, wherein the fourth polymeric layer is made of a third polymer that has the same charge as the first polymer and encapsulates the one or more composite shell layers, while the plurality of second di- or trivalent ion-containing nanoparticles adhere onto the outer surface of the fourth polymeric layer; and
   (d) a plurality of polymeric tails respectively extending from the outer surface of the outermost shell layer, wherein the plurality of polymeric tails comprise a fourth polymer.

2. The multilayer core-shell particle of claim 1, wherein the multilayer core-shell particle comprises 2 to 40 composite shell layers.

3. The multilayer core-shell particle of claim 1, wherein the functional core comprises an antimicrobial agent selected from the group consisting of, sodium fluoride, calcium fluoride, acidulated phosphate fluoride, stannous fluoride, triclosan, chlorhexidine, amikacin, gentamicin, kanamycin, neomycin, netilmicin, tobramycin, paromomycin, spectinomycin, geldanamycin, herbimycin, rifaximin, streptomycin, loracarbef, ertapenem, doripenem, imipenem, cilastatin, meropenem, cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole, teicoplanin, vancomycin, telavancin, clindamycin, lincomycin, daptomycin, azithromycin, clarithromycin, dirithromycin, erythromycin, roxithromycin, troleandomycin, telithromycin, spiramycin, aztreonam, furazolidone, nitrofurantoin, linezolid, posizolid, radezolid, torezolid, amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, penicillin G, temocillin, ticarcillin, clavulanate, sulbactam, tazobactam, bacitracin, colistin polymyxin B, ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfamethoxazole, sulfanilimide, sulfasalazine, sulfisoxazole, trimethoprim-sulfamethoxazole, sulfonamidochrysoidine, demeclocycline, doxycycline, minocycline, oxytetracycline, tetracycline, clofazimine, dapsone, capreomycin, cycloserine, ethambutol, ethionamide, isoniazid, pyrazinamide, rifampicin, rifabutin, rifapentine, streptomycin, arsphenamine, chloramphenicol, fosfomycin, fusidic acid, metronidazole, mupirocin, platensimycin, quinupristin, dalfopristin, thiamphenicol, tigecycline, tinidazole and trimethoprim.

4. The multilayer core-shell particle of claim 1, wherein the functional core comprises a whitening agent selected from the group consisting of, hydrogen peroxide, carbamide peroxide, and zinc oxide.

5. The multilayer core-shell particle of claim 1, wherein the functional core comprises an antitumor agent selected from the group consisting of, actinomycin, all-trans retinoic acid, alitretinoin, azacitidine, azathioprine, bevacizumab, bexarotene, bleomycin, bortezomib, carboplatin, capecitabine, cetuximab, cisplatin, chlorambucil, cyclophosphamide, cytarabine, daunorubicin, docetaxel, doxifluridine, doxorubicin, epirubicin, epothilone A-F, erlotinib, etoposide, fluorouracil, gemcitabine, gefitinib, hydroxyurea, idarubicin, imatinib, ipilimumab, irinotecan, mechlorethamine, melphalan, mercaptopurine, methotrexate, mitoxantrone, ocrelizumab, ofatumumab, oxaliplatin, paclitaxel, panitumab, pemetrexed, rituximab, romidepsin, tafluposide, teniposide, tioguanine, topotecan, tretinoin, valrubicin, vemurafenib, vinblastine, vincristine, vindesine, vinorelbine, vismodegib, and vorinostat.

6. The multilayer core-shell particle of claim 1, wherein the first and second di-or trivalent ion-containing nanoparticles respectively comprise a material selected from the group consisting of hydroxyapatite, fluoroapatite, calcium phosphate, calcium fluoride, zinc oxide, silicate, titanium oxide and a combination thereof.

7. The multilayer core-shell particle of claim 1, wherein at least one of the first, second and third polymers is a cationic polymer selected from the group consisting of, polyarginine, polylysine, polyhistidine, poly-ornithine, polyethyleneimine, polypropyleneimine, poly(allylamine), polystyrene-maleic acid, gelatin, and chitosan.

8. The multilayer core-shell particle of claim 1, wherein at least one of the first, second and third polymers is an anionic polymer selected from the group consisting of, polyacrylic acid, polymethacrylic acid, polycrotonic acid, polyaspartic acid, polyglutamic acid, polylactic acid, poly(lactic-co-glycolic) acid, hyaluronic acid, alginic acid, polystyrene sulfonate, carrageenan, poly(methylene-co-guanidine), polyphosphoric acid, and pamidronic acid.

9. The multilayer core-shell particle of claim 1, wherein the fourth polymer is selected from the group consisting of, polyarginine, polylysine, polyhistidine, poly-ornithine, polyethyleneimine, polypropyleneimine, poly(allylamine), polystyrene-maleic acid, gelatin, chitosan, polyacrylic acid, polymethacrylic acid, polycrotonic acid, polyaspartic acid, polyglutamic acid, polylactic acid, poly(lactic-co-glycolic) acid, hyaluronic acid, and alginic acid, polystyrene sulfonate, carrageenan, poly(methylene-co-guanidine), polyphosphoric acid, or pamidronic acid, xanthan gum, polycarbophil, poly(methylvinyl ether-co-maleic anhydride), shellac, agar, pectin, polyvinyl acetate phthalate, guar gum, polyethylene glycol, dextrin, polydextrose, and polyethylene oxide.

10. The multilayer core-shell particle of claim 1, wherein the total thickness of the one or more composite shell layers and the outermost shell is about 0.5 to 1,000 nm.

11. The multilayer core-shell particle of claim 1, wherein the average diameter of the multilayer core-shell particle is about 50 to 50,000 nm.

12. The multilayer core-shell particle of claim 1, wherein the multilayer core-shell particle is cubic-shaped, needle-shaped, spherical-shaped, pyramidal-shaped or polygonal cylindrical-shaped.

13. The multilayer core-shell particle of claim 1, wherein the multilayer core-shell particle is a pH-sensitive particle.

14. The multilayer core-shell particle of claim 1, wherein the functional core comprises sodium fluoride;
the first, third and fourth polymers are polyacrylic acid;
the second polymer is polyethyleneimine;
the first and second di- or trivalent ion-containing nanoparticles are respectively composite nanoparticles made of hydroxyapatite, fluoroapatite and calcium fluoride; and
the multilayer core-shell particle has 4 to 10 composite shell layers.

15. A process for preparing a multilayer core-shell particle of claim 1, and the process comprises the steps of:
(a) forming the one or more composite shell layers encapsulating the functional core, wherein each composite shell layer is formed by the steps of,
(a1) mixing the functional core with a first polymer to form a first particle, wherein the first particle has a first polymeric layer of the first polymer and encapsulates the functional core, and the first polymer and the functional core are oppositely-charged,
(a2) mixing the first particle with a plurality of first di- or trivalent ion-containing nanoparticles to form a second particle, wherein the second particle has the first di- or trivalent ion-containing nanoparticles adhering onto the outer surface of the first particle,
(a3) mixing the second particle with the first polymer to form a third particle, wherein the third particle has a second polymeric layer of the first polymer and encapsulates the second particle, and
(a4) mixing the third particle with a second polymer to form a fourth particle, wherein the fourth particle has a third polymeric layer of the second polymer and encapsulates the third particle, and the first polymer and the second polymer are oppositely-charged;
(b) forming the outermost shell layer encapsulating the one or more composite shell layers by the steps of,
(b1) mixing the fourth particle with a third polymer to form a fifth particle, wherein the fifth particle has a fourth polymeric layer of the third polymer and encapsulates the fourth particle, and the third polymer has the same charge as the first polymer, and
(b2) mixing the fifth particle with a plurality of second di- or trivalent ion-containing nanoparticles to form a sixth particle, wherein the sixth particle has the plurality of second di- or trivalent ion-containing nanoparticles adhering onto the outer surface of the fourth polymeric layer; and
(c) forming the plurality of polymeric tails respectively extending from the outer surface of the outermost shell layer by mixing the sixth particle with a fourth polymer, wherein the fourth polymer is a cationic, anionic or neutral polymer.

16. The process of claim 15, wherein the step (a) is repeated 2 to 40 times before the step (b) is performed, and thereby forms 2 to 40 composite shell layers.

17. The process of claim 15, wherein the functional core comprises an antimicrobial agent selected from the group consisting of, sodium fluoride, calcium fluoride, acidulated phosphate fluoride, stannous fluoride, triclosan, chlorhexidine, amikacin, gentamicin, kanamycin, neomycin, netilmicin, tobramycin, paromomycin, spectinomycin, geldanamycin, herbimycin, rifaximin, streptomycin, loracarbef, ertapenem, doripenem, imipenem, cilastatin, meropenem, cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole, teicoplanin, vancomycin, telavancin, clindamycin, lincomycin, daptomycin, azithromycin, clarithromycin, dirithromycin, erythromycin, roxithromycin, troleandomycin, telithromycin, spiramycin, aztreonam, furazolidone, nitrofurantoin, linezolid, posizolid, radezolid, torezolid, amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, penicillin G, temocillin, ticarcillin, clavulanate, sulbactam, tazobactam, bacitracin, colistin polymyxin B, ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfamethoxazole, sulfanilimide, sulfasalazine, sulfisoxazole, trimethoprim-sulfamethoxazole, sulfonamidochrysoidine, demeclocycline, doxycycline, minocycline, oxytetracycline, tetracycline, clofazimine, dapsone, capreomycin, cycloserine, ethambutol, ethionamide, isoniazid, pyrazinamide, rifampicin, rifabutin, rifapentine, streptomycin, arsphenamine, chloramphenicol, fosfomycin, fusidic acid, metronidazole, mupirocin, platensimycin, quinupristin, dalfopristin, thiamphenicol, tigecycline, tinidazole and trimethoprim.

18. The process of claim 15, wherein the functional core comprises a whitening agent selected from the group consisting of, hydrogen peroxide, carbamide peroxide, and zinc oxide.

19. The process of claim 15, wherein the functional core comprises an antitumor agent selected from the group consisting of, actinomycin, all-trans retinoic acid, alitretinoin, azacitidine, azathioprine, bevacizumab, bexarotene, bleomycin, bortezomib, carboplatin, capecitabine, cetuximab, cisplatin, chlorambucil, cyclophosphamide, cytarabine, daunorubicin, docetaxel, doxifluridine, doxorubicin, epirubicin, epothilone A-F, erlotinib, etoposide, fluorouracil, gemcitabine, gefitinib, hydroxyurea, idarubicin, imatinib, ipilimumab, irinotecan, mechlorethamine, melphalan, mercaptopurine, methotrexate, mitoxantrone, ocrelizumab, ofatumumab, oxaliplatin, paclitaxel, panitumab, pemetrexed, rituximab, romidepsin, tafluposide, teniposide, tioguanine, topotecan, tretinoin, valrubicin, vemurafenib, vinblastine, vincristine, vindesine, vinorelbine, vismodegib, and vorinostat.

20. The process of claim 15, wherein the first and second di- or trivalent ion-containing nanoparticles respectively comprise a material selected from the group consisting of hydroxyapatite, fluoroapatite, calcium phosphate, calcium fluoride, zinc oxide, silicate, titanium oxide and a combination thereof.

21. The process of claim 15, wherein at least one of the first, second and third polymers is a cationic polymer selected from the group consisting of, polyarginine, polylysine, polyhistidine, poly-ornithine, polyethyleneimine, polypropyleneimine, poly(allylamine), polystyrene-maleic acid, gelatin, and chitosan.

22. The process of claim 15, wherein at least one of the first, second and third polymers is an anionic polymer selected from the group consisting of, polyacrylic acid, polymethacrylic acid, polycrotonic acid, polyaspartic acid, polyglutamic acid, polylactic acid, poly(lactic-co-glycolic) acid, hyaluronic acid, alginic acid, polystyrene sulfonate, carrageenan, poly(methylene-co-guanidine), polyphosphoric acid, and pamidronic acid.

23. The process of claim 15, wherein the fourth polymer is selected from the group consisting of, polyarginine, polylysine, polyhistidine, poly-ornithine, polyethyleneimine, polypropyleneimine, poly(allylamine), polystyrene-maleic acid, gelatin, chitosan, polyacrylic acid, polymethacrylic acid, polycrotonic acid, polyaspartic acid, polyglutamic acid, polylactic acid, poly(lactic-co-glycolic) acid, hyaluronic acid, and alginic acid, polystyrene sulfonate, carrageenan, poly(methylene-co-guanidine), polyphosphoric acid, or pamidronic acid, xanthan gum, polycarbophil, poly(methylvinyl ether-co-maleic anhydride), shellac, agar, pectin, polyvinyl acetate phthalate, guar gum, polyethylene glycol, dextrin, polydextrose, and polyethylene oxide.

24. The process of claim 15, wherein
the functional core comprises sodium fluoride;
the first, third and fourth polymers are polyacrylic acid;
the second polymer is polyethyleneimine;
the first and second di- or trivalent ion-containing nanoparticles are respectively composite nanoparticles made of hydroxyapatite, fluoroapatite and calcium fluoride; and
the multilayer core-shell particle has 4 to 10 composite shell layers.

25. A pharmaceutical or health care composition, comprising,
an effective amount of the multilayer core-shell particles of claim 1, and
a pharmaceutically acceptable excipient.

26. The pharmaceutical or health care composition of claim 25, wherein the pharmaceutical or health care composition is an oral care composition.

27. The pharmaceutical or health care composition of claim 26, wherein the respective functional core of the multilayer core-shell particles comprises an antimicrobial agent selected from the group consisting of, sodium fluoride, calcium fluoride, acidulated phosphate fluoride, stannous fluoride, triclosan, and chlorhexidine.

28. The pharmaceutical or health care composition of claim 26, wherein the respective functional core of the multilayer core-shell particles comprises a whitening agent selected from the group consisting of, hydrogen peroxide, carbamide peroxide, and zinc oxide.

29. The pharmaceutical or health care composition of claim 25, wherein the pharmaceutical or health care composition is an antimicrobial composition.

30. The pharmaceutical or health care composition of claim 29, wherein the respective functional core of the multilayer core-shell particles comprises an antimicrobial agent selected from the group consisting of amikacin, gentamicin, kanamycin, neomycin, netilmicin, tobramycin, paromomycin, spectinomycin, geldanamycin, herbimycin, rifaximin, streptomycin, loracarbef, ertapenem, doripenem, imipenem, cilastatin, meropenem, cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole, teicoplanin, vancomycin, telavancin, clindamycin, lincomycin, daptomycin, azithromycin, clarithromycin, dirithromycin, erythromycin, roxithromycin, troleandomycin, telithromycin, spiramycin, aztreonam, furazolidone, nitrofurantoin, linezolid, posizolid, radezolid, torezolid, amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, penicillin G, temocillin, ticarcillin, clavulanate, sulbactam, tazobactam, bacitracin, colistin polymyxin B, ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfamethoxazole, sulfanilimide, sulfasalazine, sulfisoxazole, trimethoprim-sulfamethoxazole, sulfonamidochrysoidine, demeclocycline, doxycycline, minocycline, oxytetracycline, tetracycline, clofazimine, dapsone, capreomycin, cycloserine, ethambutol, ethionamide, isoniazid, pyrazinamide, rifampicin, rifabutin, rifapentine, streptomycin, arsphenamine, chloramphenicol, fosfomycin, fusidic acid, metronidazole, mupirocin, platensimycin, quinupristin, dalfopristin, thiamphenicol, tigecycline, tinidazole and trimethoprim.

31. The pharmaceutical or health care composition of claim 25, wherein the pharmaceutical or health care composition is an antitumor composition.

32. The pharmaceutical or health care composition of claim 31, wherein the respective functional core of the multilayer core-shell particles comprises an antitumor agent selected from the group consisting of, actinomycin, all-trans retinoic acid, alitretinoin, azacitidine, azathioprine, bevacizumab, bexarotene, bleomycin, bortezomib, carboplatin, capecitabine, cetuximab, cisplatin, chlorambucil, cyclophosphamide, cytarabine, daunorubicin, docetaxel, doxifluridine, doxorubicin, epirubicin, epothilone A-F, erlotinib, etoposide, fluorouracil, gemcitabine, gefitinib, hydroxyurea, idarubicin, imatinib, ipilimumab, irinotecan, mechlorethamine, melphalan, mercaptopurine, methotrexate, mitoxantrone, ocrelizumab, ofatumumab, oxaliplatin, paclitaxel, panitumab, pemetrexed, rituximab, romidepsin, tafluposide, teniposide, tioguanine, topotecan, tretinoin, valrubicin, vemurafenib, vinblastine, vincristine, vindesine, vinorelbine, vismodegib, and vorinostat.

33. A method for selectively inhibiting the growth or metabolism of cariogenic and/or periodontopathic microorganisms in a subject, comprising,
administering the oral care composition of claim 26 to the oral cavity of the subject; and
allowing the adhesion of the multilayer core-shell particles or the porous core-shell particles to the oral surface of the subject.

* * * * *